(12) United States Patent
Robertson et al.

(10) Patent No.: US 9,696,319 B2
(45) Date of Patent: *Jul. 4, 2017

(54) TUMOUR MARKERS

(75) Inventors: John F. R. Robertson, Nottingham (GB); Catherine R. L. Graves, Nottingham (GB); Michael R. Price, Nottingham (GB); Frances M Price, legal representative, Nottingham (GB)

(73) Assignee: Oncimmune Ltd., Nottingham (GB)

( * ) Notice: Subject to any disclaimer, the term of this patent is extended or adjusted under 35 U.S.C. 154(b) by 633 days.

This patent is subject to a terminal disclaimer.

(21) Appl. No.: 13/349,348

(22) Filed: Jan. 12, 2012

(65) Prior Publication Data

US 2012/0115749 A1 May 10, 2012

Related U.S. Application Data

(63) Continuation of application No. 11/953,237, filed on Dec. 10, 2007, now Pat. No. 8,114,604, which is a continuation of application No. 09/700,092, filed as application No. PCT/GB99/01479 on May 11, 1999, now Pat. No. 7,402,403.

(30) Foreign Application Priority Data

May 11, 1998 (GB) .................................. 9810040.7

(51) Int. Cl.
| | |
|---|---|
| *C40B 30/04* | (2006.01) |
| *G01N 33/566* | (2006.01) |
| *G01N 33/574* | (2006.01) |
| *G01N 33/68* | (2006.01) |
| *C07K 14/47* | (2006.01) |
| *C12Q 1/68* | (2006.01) |

(52) U.S. Cl.
CPC ..... *G01N 33/6854* (2013.01); *C07K 14/4748* (2013.01); *G01N 33/574* (2013.01); *C12Q 1/6886* (2013.01); *G01N 2800/52* (2013.01); *Y10S 436/813* (2013.01)

(58) Field of Classification Search
None
See application file for complete search history.

(56) References Cited

U.S. PATENT DOCUMENTS

| | | |
|---|---|---|
| 4,241,044 A | 12/1980 | Kim |
| 4,898,951 A | 2/1990 | Symons |
| 4,937,185 A | 6/1990 | Webb et al. |
| 5,110,911 A | 5/1992 | Samuel et al. |
| 5,157,020 A | 10/1992 | Kay et al. |
| 5,501,955 A | 3/1996 | Bergman |
| 5,561,049 A | 10/1996 | Vold et al. |
| 5,652,115 A | 7/1997 | Marks et al. |
| 5,721,105 A | 2/1998 | Bergmann |
| 5,726,023 A | 3/1998 | Cheever et al. |
| 5,747,268 A | 5/1998 | Herring et al. |
| 5,763,164 A | 6/1998 | Calenoff |
| 5,827,666 A | 10/1998 | Finn et al. |
| 5,876,728 A | 3/1999 | Kass et al. |
| 5,885,793 A | 3/1999 | Griffiths et al. |
| 6,187,306 B1 | 2/2001 | Pardoll et al. |
| 6,280,962 B1 | 8/2001 | Cohen |
| 6,322,989 B1 | 11/2001 | Cohen |
| 6,387,639 B1 | 5/2002 | Posner et al. |
| 6,475,804 B1 | 11/2002 | Lohse |
| 6,645,465 B2 | 11/2003 | Hanash |
| 6,667,160 B2 | 12/2003 | Fine |
| 7,205,117 B1 | 4/2007 | Robertson et al. |
| 7,282,345 B1 | 10/2007 | Hancock et al. |
| 7,402,403 B1 | 7/2008 | Robertson et al. |
| 8,114,604 B2 | 2/2012 | Robertson et al. |
| 8,574,848 B2 | 11/2013 | Robertson et al. |
| 8,592,169 B2 | 11/2013 | Robertson et al. |
| 2002/0168696 A1 | 11/2002 | Hanash |
| 2003/0008332 A1 | 1/2003 | Ryan et al. |
| 2003/0049692 A1 | 3/2003 | Latov et al. |
| 2003/0099639 A1 | 5/2003 | Rikihisa et al. |
| 2003/0138860 A1 | 7/2003 | Robertson et al. |
| 2003/0232399 A1 | 12/2003 | Robertson et al. |
| 2005/0084904 A1 | 4/2005 | Laal et al. |

(Continued)

FOREIGN PATENT DOCUMENTS

| | | |
|---|---|---|
| EP | 0236606 | 6/1992 |
| EP | 0684477 | 11/1995 |

(Continued)

OTHER PUBLICATIONS

Vennegoor et al (Cancer Letter, 1997, vol. 116, pp. 93-101).*
Lenner et al (British Journal of Cancer, Feb. 1999, vol. 79, pp. 927-932).*
Regidor et al (European Journal of Gynaecological Oncology, 1996, vol. 17, pp. 192-199).*
Graves et al, Journal of Peptide Research, 2005, vol. 66, pp. 357-363.*
Storr et al, Glycobiology, 2000, vol. 10, pp. 439-449.*
Notice of Allowance dated Jul. 9, 2013 in U.S. Appl. No. 10/534,773, 10 pages.
Final Office Action dated Jul. 3, 2013 in U.S. Appl. No. 11/681,830, 18 Pages.
Non-Final Office Action dated May 23, 2013 in U.S. Appl. No. 11/814,516, 9 pages.

(Continued)

*Primary Examiner* — Karen Canella
(74) *Attorney, Agent, or Firm* — Finnegan, Henderson, Farabow, Garrett & Dunner, L.L.P.

(57) ABSTRACT

A method of determining the immune response of a mammal to circulating tumor marker proteins is described in which a sample of bodily fluid, for example plasma or serum, is contacted with a panel of two or more distinct tumor marker antigen. The presence of complexes between the tumor marker antigens and any autoantibodies to the antigens present in the sample are detected and provide an indication of an immune response to a circulating tumor marker protein. The method is useful for the diagnosis of cancer, particularly for identifying new or recurrent cancer in an otherwise assymptomatic patient.

27 Claims, 15 Drawing Sheets

(56) References Cited

U.S. PATENT DOCUMENTS

Figure 2:
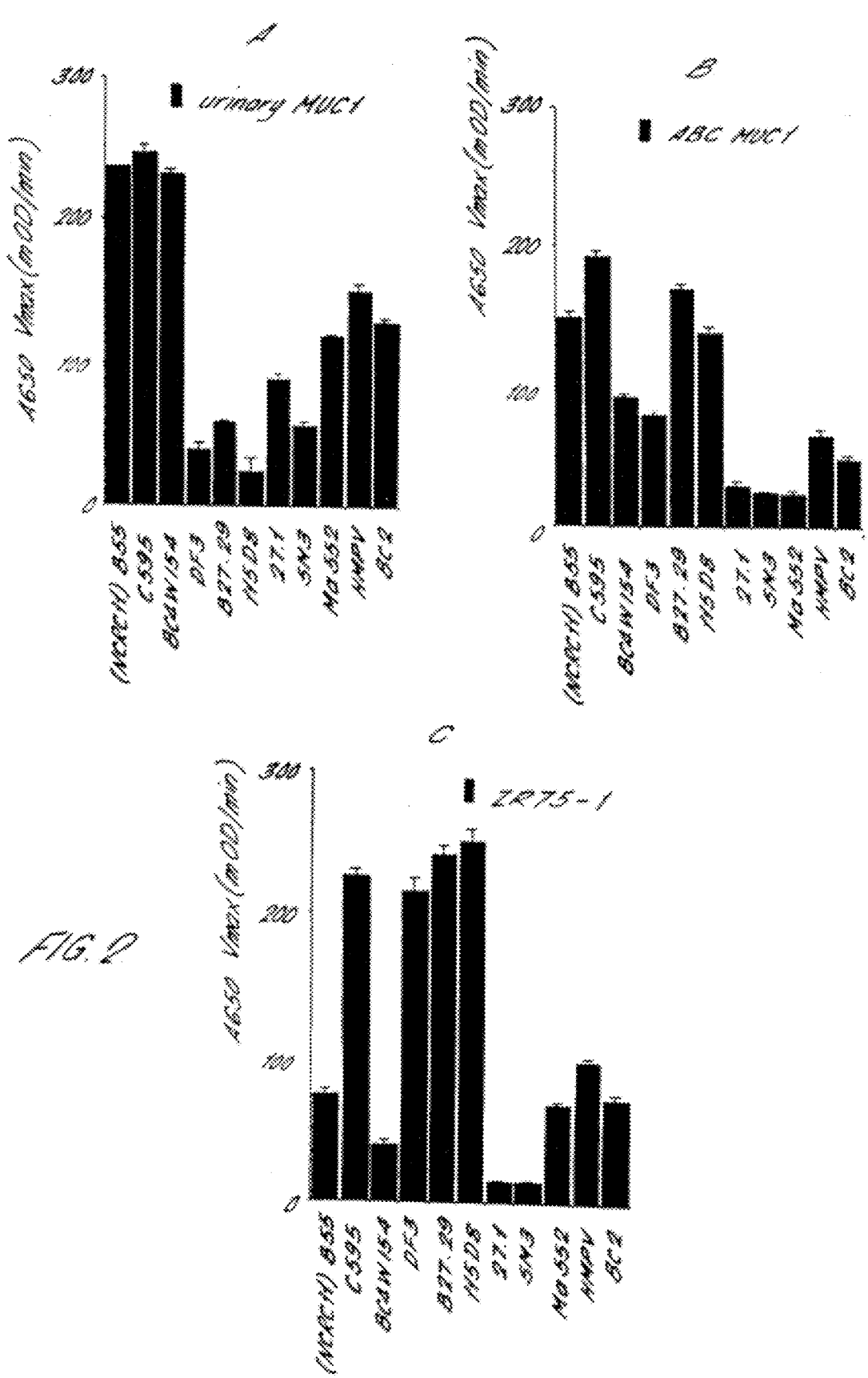

| | | | |
|---|---|---|---|
| 2005/0276485 A1 | 12/2005 | Mori et al. | |
| 2006/0141547 A1 | 6/2006 | Das et al. | |
| 2007/0172487 A1 | 7/2007 | Shih et al. | |
| 2007/0224174 A1 | 9/2007 | Kang et al. | |
| 2008/0108084 A1 | 5/2008 | Robertson et al. | |
| 2008/0153113 A1 | 6/2008 | Robertson et al. | |
| 2008/0213921 A1 | 9/2008 | Robertson et al. | |
| 2008/0305476 A1 | 12/2008 | Robertson et al. | |
| 2009/0176319 A1 | 7/2009 | Robertson et al. | |
| 2011/0086061 A1 | 4/2011 | Robertson et al. | |
| 2013/0090251 A1 | 4/2013 | Robertson et al. | |
| 2014/0038212 A1 | 2/2014 | Robertson et al. | |

FOREIGN PATENT DOCUMENTS

| | | |
|---|---|---|
| EP | 1200832 | 5/2006 |
| GB | 2395270 | 5/2004 |
| GB | 2426581 | 11/2006 |
| GB | 2007003486 | 9/2007 |
| GB | 2007003486 | 12/2007 |
| JP | 7294530 | 11/1995 |
| JP | 9189702 | 7/1997 |
| JP | 09229933 A | 9/1997 |
| JP | 11-230966 | 8/1999 |
| WO | 8901153 | 2/1989 |
| WO | 9213065 | 8/1992 |
| WO | 9311236 | 6/1993 |
| WO | 9321529 | 10/1993 |
| WO | 9423728 | 10/1994 |
| WO | 9600084 | 1/1996 |
| WO | 9603502 | 2/1996 |
| WO | 9711715 | 4/1997 |
| WO | 9714794 | 4/1997 |
| WO | 9855872 | 6/1998 |
| WO | 9958978 | 11/1999 |
| WO | 9958979 | 11/1999 |
| WO | WO 99/66332 | 12/1999 |
| WO | 0026668 | 5/2000 |
| WO | 0034787 | 6/2000 |
| WO | 0111372 | 2/2001 |
| WO | 02059617 | 8/2002 |
| WO | 2004044590 | 5/2004 |
| WO | 2006126008 | 11/2006 |
| WO | 2008032084 | 3/2008 |

OTHER PUBLICATIONS

Notice of Allowance dated May 30, 2013 in U.S. Appl. No. 11/854,050, 6 pages.
Final Office Action dated Jun. 5, 2013 in U.S. Appl. No. 12/343,047, 24 pages.
Hirasawa et al., "KL-6, a human MUC1 mucin, is chemotactic for human fibroblasts.", American Journal of Respiratory Cell and Molecular Biology [1997, 17(4):501-507].
Sakurai et al., "Differential expression of the glycosylated forms of MUC1 during lung development", European Journal of Histochemistry 2007, vol. 51 issue 2 (Apr.-Jun.); 95-102.
U.S. Appl. No. 10/534,773 , "Final Office Action", Feb. 22, 2013, 11 pages.
U.S. Appl. No. 11/681,830 , "Non-Final Office Action", Dec. 5, 2012, 19 pages.
U.S. Appl. No. 12/343,047 , "Non-Final Office Action", Nov. 26, 2012, 19 pages.
U.S. Appl. No. 13/438,344 , "Non-Final Office Action", Mar. 20, 2013, 7 pages.
Harlow et al., "Antibodies: A Laboratory Manual", Cold Spring Harbor Laboratory, 1988, 562-563.
Kohno et al., "Detection of Soluble Tumor-associated Antigens in Sera and Effusions Using Novel Monoclonal Antibodies, KL-3 and KL-6, against Lung Adenocarcinoma", Jpn. J. Clin. Oncol. 18: 203-216, 1988.
Definition of "monocyte" in On-line Medical Dictionary downloaded on Feb. 5, 2005 from url. www.cancerweb.ncl.ac.uk.
"Cell and Molecular Biology of Vertebrate Hard Tissues", Ciba Foundation Symposium 136.
"GB0725239.8 Search Report dated Apr. 24, 2008".
"National Library of Medicine Gateway MeSH term definition downloaded from the Web", Apr. 23, 2009.
"Patent Abstracts of Japan", Nov. 28, 1997, vol. 097, No. 11.
"PCT/GB2008/004260 International Search Report and Written Opinion, mailed Feb. 27, 2009".
Aaronson, S. A. et al., "Characterization of Murine Sarcoma Virus (KIRSTEN) Transformation of Mouse and Human Cells", J. Gen. Virol., 1971, 13: 245-252; ATCC accession No. CRL 1569, 245-252.
Agrawal, et al., "Cancer-associated MUC1 mucin inhibits human T-cell proliferation, which is reversible by IL-2", Nature Medine, Jan. 1998, 4(1):43-49.
Ambrosini, G. et al., "A novel anti-apoptois gene lymphoma, survivin, expressed in cancer and lymphone", Nature Med, 1997, 3(8), 917-21.
Angelopoulou, K. et al., "Detection of the TP53 Tumour Suppressor Gene Product and p53 Auto-antibodies in the Ascites of Women with Ovarian Cancer", European Journal of Cancer, Jan. 1997, Pergamon Press, Oxford, GB, vol. 33, No. 1, 115-121.
Anker, et al., "K-ras mutations are found in DNA extracted from the plasma of patients with colorectal cancer", Gastroenterology, Apr. 1997, vol. 112, No. 4, 1114-1119.
Aparecida, et al., "Value of CEA Level Determination in Gallbladder Bile in the Diagnosis of Liver Metastases Secondary to Colorectal Adenocarcinoma", Sao Paulo Medical Journal, 2001, vol. 119, No. 3, 110-113.
Apostolopoulos, et al., "MUC1 Cross-reactive Gala(1,3)GAL antibodies in humans switch immune responses from cellular to humoral", Nature Medicine, 1998, vol. 4, 315-320.
Asano, et al., "Presence of anti-AFT-antibody producing B cells in peripheral blood lymphocyte of hepatocellular carcinoma patient", Nippon Shokakibyo Gakkai Zasshi, Feb. 1984, 81(2):278.
Ayala, A. R. et al., "Human Chorionic Gonadotropin Immunoreactivity in Serum of Patients With Malignant Neoplasms", Am J Reprod Immuno., Apr.-May 1983, 3(3), 149-51.
Baechstrom, et al., "Purification and Characterization of Sialyl-Le—Carrying Mucins of Human Bile; Evidence for the Presence of MUC1 and MUC3 Apoproteins", The Journal of Biological Chemistry, 1994, vol. 269, No. 2, 14430-14437.
Barak, V. et al., "Clinical utility of cytokeratins as tumor markers", Clin Biochem, Jul. 2004, 37(7), 529-40.
Barrette, Roger W. et al., "Quantifying Specific Antibody Concentrations by Enzyme-Linked Immunosorbent Assay Using Slope Correction", Clinical and Vaccine Immunology, Jul. 2006, vol. 13, No. 7, 802-805.
Baselga, J. et al., "Phase II Study of Weekly Intravenous Recombinant Humanized Anti-p185 HER2 Monoclonal Antibody in Patients with HER2/neu-Overexpressing Metastatic Breast Cancer", J. Clin Oncol., 1996, 14(3), 737-744.
Batra, S. K. et al., "Expression of the Human MUC1 Mucin cDNA in a Hamster Pancreatic Tumor Cell Line HP-1", Int. J. Pancreatology, 1992, 12:271-283.
Beatty, et al., "Biochemical Characterization of the Soluble Form of Tumor Antigen MUC1 Isolated from Sera and Ascites Fluid of Breast and Pancreatic Cancer Patients", Clinical Cancer Research, 2001, vol. 7, 781-787.
Beatty, J. D. et al., "Measurement of monoclonal antibody affinity by non-competitive enzyme immunoassay", Journal of Immunological Methods, 1987, 100, pp. 173-179.
Bellone, et al., "Cancer immunotherapy: synthetic and natural peptides in the balance", Immunology Today, 1999, 20, pp. 457-462.
Ben-Efraim, "One Hundred Years of Cancer Immunotherapy: A Critical Appraisal", Tumor Biology, 1999, vol. 20(1), pp. 1-24.
Ben-Mahrez, et al., "Detection of circulating antibodies against of c-myc protein in cancer patient sera", British Journal of Cancer, 1988, 37:529-534.

(56) References Cited

OTHER PUBLICATIONS

Bhatti, et al., "Circulating Immunobiologic Markers in Prostatic Cancer and their Modulation by Surgical/Hormonal Therapy", Journal of Tumor Marker Oncology, Summer-1994, vol. 9(2) 125-131.

Blackwood, Elizabeth M. et al., "Functional Analysis of the AUG- and CUG-Initiated Forms of the c-Myc Protein", Molecular Biology of the Cell, 1994, 5: 597-609, 597-609.

Block, T. M. et al., "Use of targeted glycoproteomics to identify serum glycoproteins that correlate with liver cancer in woodchucks and humans", Proc Natl Acad Sci USA, Jan. 18, 2005, 102(3), 779-84.

Booyse, F. M. et al., "Isolation and characterization of a urokinase-type plasminogen activator (MR=54,000) from cultured human epithelial cells indistinguishable from urinary urokinase", J Biol Chem, 1984, 259(11), 7198-205.

Braun, S. et al., "Cytokeratin-Positive Cells in the Bone Marrow and Survival of Patients with Stage I, II, or III Breast Cancer", N Engl J. Med, 2000, 342:8, 525-533.

Brichory, et al., "An Immune Response Manifested by the Common Occurrence of Annexins I and II Autoantibodies and High Circulating Levels of IL-6 in Lung Cancer", PNAS, 2001, 98(17):9824-9829.

Butler, W. T. et al., "Osteopontin—Structure and biological activity", CBA Foundation Symposia, 1988, 136, 203-206.

Byers, "What can randomized controlled trials tell us about nutrition and cancer prevention?", CA Cancer Journal, Nov./Dec. 1999, vol. 49, No. 6, pp. 353-361.

Callans, L. S. et al., "Raf-1 Protein Expression in Human Breast Cancer Cells", Ann Surg Oncol, Jan. 1995, 2(1):38-42.

Canevari, et al., "1975-1995 Revised anti-cancer serological response: Biological significance and clinical implications", Annals of Oncology, 1996, vol. 7, pp. 227-232.

Capella, G. et al., "Frequency and Spectrum of Mutations at Codons 12 and 13 of the C-K-ras Gene in Human Tumors", Environ Health Perspective, 1991, 93: 125-131.

Carlsson, Hans E., "Titration of antibodies to Salmonella O Antigens by Enzyme-Linked Immunosorbent Assay", Infection and Immunity, Nov. 1972, vol. 6, No. 5, 703-708.

Casiano, C. A. et al., "Tumor-associated Antigen Arrays for the Serological Diagnosis of Cancer", Molecular & Cellular Proteomics, 2006, 1745-1759.

Cervello, M. et al., "Cyclooxygenases in hepatocellular carcinoma", World J. Gastroenterol, Aug. 28, 2006, 12(28), 5113-5121.

Chapman, C. et al., "Autoantibodies in breast cancer: their use as an aid to early diagnosis", Annals of Oncology, Mar. 7, 2007, vol. 18, 868-873.

Chapman, C. J. et al., "Autoantibodies in lung cancer: posibilities for early detection and subsequent cure", Thorax, Sep. 26, 2007, 0:1-6. doi:10.1136/thx.2007.083592.

Chari, S. et al., "Partial-Purification of Inhibition from Human Testicular Extracts", ACTA Endocrinologia, 1977, 85 Suppl 212, 215-219.

Chen, Y. T., "A testicular antigen aberrantly expressed in human cancers detected by autologous antibody screening", Proc. Natl. Acad. Sci, 1997, 94, 1914-1918.

Chinni, R. S. et al., "Humoral Immune Responses to Cathepsin D and Glucose-regulated Protein 78 in Ovarian Cancer Patients", Clinical Cancer Research, Sep. 1997, 3, 1557-1564.

Clemmensen, I. et al., "Purification and characterization of a novel, oligomeric, plasminogen kringle 4 binding-proetein from human plasma-tetranectin", Eur J. Biochem, 1986, 156(2), 237-333.

Coomber, et al., "Characterisation and clinicopathological correlates of serum anti-p53 antibodies in breast and colon cancer", J Cancer Res Clin Oncol, 1996, 122(12):757-62.

Coussens, L. et al., "Tyrosine kinase receptor with extensive homology to EGF receptor shares chromosomal location with neu oncogene", 1985, 230, 1132-1139.

Croce, et al., "Expression of monoclonal-antibody-defined antigens in fractions isolated from human breast carcinomas and patient's serum", Cancer. Immunol. Immunother., 1995, vol. 40, 132-137.

Dahlberg, T., "Enzyme-Linked Immunosorbent Assay for Titration of Haemophilus influenzae Capsular and O Antigen Antibodies", Journal of Clinical Microbiology, Aug. 1980, vol. 12, No. 2, 185-192.

Deguchi, et al., "Autoantibody to Human c-myc Oncogene Product in Autoimmune Patient's Sera", Int. Arch. Allergy Appl. Immunol., 1988, vol. 87, 313-316.

Denton, et al., "Induction of antibody responses to breast carcinoma associated mucins using synthetic peptide constructs as immunogens", Cancer Letters, 1993, vol. 70, 143-150.

Desouza, B. et al., Oncogene, 1993, 8:1797-1806.

Devine, P. L. et al., "Circulating Mucins as Tumor Markers in Ovarian Cancer (Review)", Anticancer Res., May-Jun. 1992, 12(3), 709-17.

Diamandis, E. et al., "Immunoassay", Academic Press, San Diego, CA, 1996.

Diamandis, E. P. , "Human tissue kallikrein gene family: applications in cancer", Cancer Lett, Jun. 2005, 224(1), 1-22.

Diamandis, E. P. et al., "Human Tissue Kallikreins: A Family of New Cancer Biomarkers", Clin. Chem, Aug. 2002, 48(8), 1198-1205.

Diamandis, E. P. et al., "The new human kallikrein gene family: implications in carcinogenesis", Trends Endocrinol Metab, Mar. 2000, 11(2), 54-60.

Disis, et al., "High-Titer HER-2/neu Protein-Specific Antibody Can be Detected in Patients with Early-Stage Breast Cancer", Journal of Clinical Oncology, 1997, vol. 15, 3363-3367.

Downward, et al., "Close similarity of epidermal growth factor receptor and v-erb-B oncogene protein sequences", Nature, 1984, 307, 521-527.

Dsouza, B. et al., "Collagen-induced morphogenesis and expression of the a2-integrin subunit is inhibited in c-erbB2-transfected human mammary epithelial cells", Oncogene, 1993, 8, 1797/1806.

Duffy, M. J., "Carcinoembryonic antigen", Clin. Chem, Apr. 2001, 47(4), 624-30.

Ellis, I. O. et al., "A monoclonal antibody, NCRC-11, raised to human breast carcinoma. 1. Production and immunohistological characterization", Histopathology, 1984, 8: 501-516.

Fateh-Moghadam, et al., "Sensible use of tumour markers", Verlag GMBH, ISBN 3-926725-07-09, 1993.

Fernandez-Madrid, F., "Autoantibodies to Annexin XI-A and Other Autoantigens in the Diagnosis of Breast Cancer", Cancer Research, 2004, 64, 5089-5096.

Fishman, P. et al., "Application of autoantibodies to cancer therapy: A new concept", The 9th International Congress of Immunology, 1995, 664.

Fossa, A. et al., "Identification of a nucleolar protein No55 as a tumour-associated auto-antigen in patients with prostate cancer", Br J Cancer, 2000, 83(6), 743-9.

Frazer, "Is vaccine therapy the future in cancer prevention?", Expert Opinion on Pharmacotherapy, 2004, 5(12), pp. 2427-2434.

Gasperi-Campani, et al., "Chromosomal alterations, biological features and in vitro chemosensitivity of SCLC-R1, a new cell line from human metastatic small cell lung carcinoma", European Journal of Cancer, Apr. 1998, vol. 34, No. 5, 724-730.

Gerke, V., "Annexins: From Structure to Function", Physiological Reviews, 2002, 82, 331-371.

Giardina, P. C., "Effect of antigen coating . . . ", Clin. Diagnostic Lab. Immunol., 2003, vol. 10, 1136-1140.

Gnudi, L. et al., "Adenovirus-Mediated Gene Transfer of Dominant Negative Rasasn17 in 3T3L 1 Adipocytes Does Not Alter Insulin-Stimulated PI3-Kinase Activity of Glucose Transport", Mol. Endocrinol., 1997, 11, 67-76.

Gourevitch, et al., "Polymorphic epithelial mucin (MUC-1)-containing circulating immune complexes in carcinoma patients", British Journal of Cancer, Oct. 1995, 72, 934-938.

Goydos, J. S. et al., "A Phase I Trial of a Synthetic Mucin Peptide Vaccine", J. Surgical Res., 1996, 63: 298-304.

(56) References Cited

OTHER PUBLICATIONS

Graham, R. A. et al., "The polymorphic epithelial mucin: potential as an immunogen for a cancer vaccine", Cancer Immunol. Immunother, 1996, 42:71-80.
Granziero, et al., "Adoptive immunotherapy prevents prostate cancer in a transgenic animal model", Eur J Immunol., Apr. 1999, vol. 29(4), pp. 1127-1138.
Green, et al., "Serum p53 Auto-antibodies: Incidence in Familial Breast Cancer", European Journal of Cancer, 1994, vol. 30A, 580-584.
Gregory Jr, J. J. et al., "Alpha-Fetoprotein and beta-Human Chorionic Gonadotropin. Their Clinical Significance as Tumour Markers", Drugs, Apr. 1999, 57(4), 463-7.
Griffiths, B. et al., "Assignment of the polymorphic intestinal mucin gene MUC2 to chromosome-11p15", Ann Hum Genet, 1990, 54:277-85.
Gure,, "Human Lung Cancer Antigens Recognized by Autologous Antibodies: Definition of a Novel cDNA Derived from the Tumor Suppressor Gene Locus on Chromosome 3p21.3", Ludwig Institute for Cancer Research, 1998, 1034-1040.
Haga, Y. et al., "Partial Purification and Characterization of CA19-9 Antigen from the Ascitic Fluid of a Patient with Pancreatic Cancer", Clin Biochem, Oct. 22, 1989, (5)363-8.
Harlow, E. et al., "Antibodies: A Laboratory Manual", Cold Spring Harbor Laboratory, 1988, 211-227.
Hayes, D. F., "Serum tumor markers for breast cancer", Anticancer Drugs, Abstract, 1995, vol. 6, suppl. 2, 26-27 (Abstract).
He, Ping et al., "Proteomics-based identification of alpha-enolase as a tumor antigen in non-small lung cancer", Cancer Sci, Aug. 2007, 98(8), 1234-1240.
Hehir, Dermot J. et al., "C-myc Oncogene Expression: A Marker for Females at Risk of Breast Carcinoma", Journal of Surgical Oncology, 1993, vol. 54, 207-210.
Hill, et al., "Nature of Carcinoembryonic Antigen Purified from Malignant Ascitic Fluid of Serous Cystadenocarcinoma of the Ovary", Molecular Immunology, 1981, vol. 18, No. 7, 647-653.
Hinoda, Y. et al., "Detection of a Circulating Antibody Against a Peptide Epitope on a Mucin Core Protein, MUC1, in Ulcerative Colitis", Dept. of Internal Medicine (Section 1), Sapporo Medical College S-1, W-16, Sapporo, Japan, 1991, 163-168.
Hirasawa, et al., "Natural Autoantibody to MUC1 Is a Prognostic Indicator for Non-Small Cell Lung Cancer", Am J Respir Crit Care Med, 2000, 161:589-594.
Houghton, et al., "Detection of Cell Surface and Intracellular Antigens by Human Monoclonal Antibodies—Hybrid Cell Lines Derived from Lymphocytes of Patients with Malignant Melanoma", J. Exp. Med., Jul. 1983, vol. 158, 53-65.
Hsu, W. M. et al., "GRP78 expression correlates with histologic differentiation and favorable prognosis in neuroblastic tumors", Int J Cancer, Mar. 1, 2005, 113, 920-7.
Hudelist, G. et al., "Use of high-throughput protein array for profiling of differentially expressed proteins in normal and malignant breast tissue", Breast Cancer Res treat., Aug. 2004, vol. 86(3), 281-91.
Hudson, Gail A. et al., "Method for Testing Antiserum Titer and Avidity in Nephelometric Systems", Clinical Chemistry, 1981, vol. 27, No. 11, 1838-1844.
Huhtala, M. L. et al., "Excretion of a tumor associated trypsin-inhibitor (TATI) in urine of patients with Gynecological Malignancy", Int J Cancer, 1983, vol. 31(6), 711-714.
Ibrahim, S. O. et al., "Expression of biomarkers (p53, transforming growth factor alpha, epidermal growth factor receptor, c-erbB-2/neu and the proliferative cell nuclear antigen) in oropharyngeal squamous cell carcinomas", Oral Oncology, Elsevier Science, Oxford, GB, May 1999, 35(3):302-313.
Israeli, R. S., "Molecular Cloning of a Complementary DNA Encoding a Prostate-specific Membrane Antigen", Cancer Res., 1993, 53:227-30.
Jager, D., "Cancer-Testis Antigens and ING1 Tumor Suppressor Gene Product Are Breast Cancer Antigens: Characterization of Tissue-Specific ING1 Transcripts and a Homologue Gene", Cancer Res, Dec. 15, 1999, vol. 59(24), 6197-6204.
Jager, D. et al., "Identification of a tissue-specific putative transcription factor in breast tissue by serological screening of a breast cancer library", Cancer Res, 2001, vol. 61(5), 2055-61.
Jais, et al., "Association of Serum Antibodies against p53 protein with poor survival in patients with Zollinger-Ellison syndrome", Gastroenterology, Elsevier, Philadelphia, PA, Jan. 1998, vol. 114, No. 1, 37-43.
Jalanko, et al., "Immunochemical properties of alpha-fetoprotein (AFP) and antibodies to autologous AFT", Immunol. Commun, 1978, vol. 7, No. 2, 209-222.
Janeway, et al., Immunobiology, 5th ed., 2001.
Janeway, et al., "Competitive Inhibition Assay for Antigen in Unknown Samples", Immunobiology downloaded from url www.ncbi.nlm.nih.gov/books/bv.fcgi?rid=imm.figgrp.2410, 2001, total 2 pages.
Jerome, K. R. et al., "A Survivor of Breast Cancer with Immunity to MUC-1 Mucin, and Lactational Mastitis", Cancer Immunology and Immunotherapy, Jan. 1997, Berlin, DE, vol. 43, No. 6, 355-360.
Karanikas, et al., "Antibody and T Cell Responses of Patients with Adenocarcinoma Immunized with Mannan-MUC1 Fusion Protein", J. Clin Invest., 1997, vol. 100, No. 11, 2783-2792.
Karlan, B. Y. et al., "Peritoneal Serous Papillary Carcinoma, A Phenotypic Variant of Familial Ovarian Cancer: Implications for Ovarian Cancer Screening", American Journal of Obstetrics & Gynecology, Apr. 1999, Mosby, St. Louis, MO, vol. 180, No. 4, 917-928.
Kasof, G. M. et al., "Livin, a novel inhibitor of apoptosis protein family", J Biol Chem, 2000, vol. 276(5), 3238-46.
Kawahara, "Use of Four Monoclonal Antibodies to Detect Tumor Markers", Cancer, 1986, vol. 58, 2008-2012.
Kiefer, M. C. et al., "The CDNA and derived amino-acid sequence for human Osteopontin", Nucleic Acids Res, 1989, 17(8), 3306.
Kim, H. et al., "Human kallikrein gene 5 (KLK5) expression is an indicator of poor prognosis in ovarian cancer", Br. J. Cancer, 2001, vol. 84(5), 643-650.
Kim, M. J. et al., "Clinicopathologic significance of the basal-like subtype of breast cancer: a comparison with hormone receptor and Her2/neu-overexpressing phenotypes", Hum Pathol.—Rpub Jul. 18, 2006, Sep. 2006, 37(9), 1217-26.
Kirchoff, C., "A major human epididymis-specific cDNA encodes a protein with sequence homology to extracellular proteinase-inhibitors", Biology of Reproduction, 1991, 45(2), 350-357.
Kotera, et al., "Humoral Immunity against a Tandem Repeat Epitope of Human Mucin MUC-1 in Sera from Breast, Pancreatic, and Colon Cancer Patients", Cancer Research, 1994, vol. 54, 2856-2860.
Krause, P. et al., "SeroGRID: an improved method for the rapid selection of antigens with disease related immunogenicity", J Immunol Methods, Dec. 2003, vol. 283, 261-7.
Kumar, S. et al., "Standardisation and comparison of serial dilutions and single dilution enzyme linked immunosorbent assay (ELISA) using different antigenic preparations of the Babesia (Theileria) equi parasite", Veterinary Research, 2003, vol. 34, No. 1 abstract, 71-83.
Kuralay, et al., "Diagnostic Usefulness of Tumour Marker Levels in Pleural Effusions of Malignant and Benign Origin", Clinica Chimica Acta, 2000, vol. 300, 43-55.
Kutteh, W. H. et al., "Immunologic Characterization of Tumor Markers in Human Ovarian Cancer Cell Lines", Journal of the Society for Gynecological Investigation, 1996, vol. 3, No. 4, 216-222.
Laeng, et al., "Anti-Neural Autoantibodies, types 1 and 2: Their Utility in the Study of Tumors of the Nervous System", Acta Neuropathol, 1998, 329-339.
Lafond, R. E. et al., "Autoantibodies to c-myc protein: elevated levels in patients with African Burkitt's lymphoma and norman Ghanians", Autoimmunity, 1992, vol. 13, No. 3, 215-224.
Lai, et al., "Presence of Serum Anti-P53 Antibodies is Associated with Pleural Effusions and Poor Prognosis in Lung Cancer Patients", Clinical Cancer Research, 1998, vol. 4, 3025-3030.

(56) References Cited

OTHER PUBLICATIONS

Lawniczak, et al., "The Search for Tumor-Associated Proteins in Pleural Effusions by Means of Moniclonal Antibodies and a Dot Blot Assay", Lung, 1992, vol. 170, 65-74.
Lederman, Seth et al., "A Single Amino Acid Substitution in a Common African Allele of the CD4 Molecule Ablates Bingin of the Monoclonal Antibody, OCT4", Molecular Immunology 1991, vol. 28, No. 11, 1171-1181.
Li, Choh H. et al., "B-Endorphin omission analogs: Dissociation of immunoreactivity from other biological activities", Proc. Natl. Acad. Sci., Jun. 1980, vol. 77, No. 6, 3211-3214.
Lindner, P. et al., "Specific Detection of His-Tagged Proteins with Recombinant Anti-His Tag scFv-Phosphatase or scFv-Phage Fusions", Bio Techniques, 1997, 22 (1), 140-149.
Lloyd, K. O. et al., "Isolation and Characterization of Ovarian Cancer Antigen CA 125 Using a New Monoclonal Antibody (VK-8) Identification as a Mucin-Type Molecule", Int. J. Cancer, 1997, 71: 842-850.
Lubin, et al., "Analysis of p53 Antibodies in Patients with Various Cancers Define B-Cell Epitopes of Human p53: Distribution on Primary Structure and Exposure on Protein Surface", Cancer Research, 1993, vol. 53, pp. 5872-5876.
Luo, et al., "Identification of Heat Shock Protein 90 and Other Proteins as Tumour Antigens by Serological Screening of an Ovarian Carcinoma Expression Library", British Journal of Cancer, 2002, 339-343.
Maeda, A. et al., "Aberrant Expression of Photoreceptor-specific Calcium-binding Protein (Recoverin) in Cancer Cell Lines", Cancer Res. 2000, Apr. 1, 2000, 60(7):1914-20.
Mashino, K. et al., "Expression of multiple cancer-testis antigen genes in gastrointestinal and breast carcinomas", Br. J. Cancer, 2001, 85(5):713-720.
Matlashewski, G. et al., "Isolation and characterization ofa human p53 cDNA clone: expression of the human p53 gene.", EMBO J., 1984, 3:3257-3262.
McIntyre, et al., "Oral contraceptive usage and the expression of CA 15-3 and C-erB-2 in the saliva of healthy women", Oral Radiology and Endodontics, Dec. 1999, vol. 88, No. 6, 687-690.
Meichenin, M. et al., "Tk, a new colon tumor-associated antigen resulting from altered O-glycosylation", Cancer Res, Oct. 1, 2000, 60 (19), 5499-507.
Mercer, D. W , "Use of Multiple Markers to Enhance Clinical Utility", Immunology Series, 1990, vol. 53, 39-54.
Microbix Biosystems Inc., "Antigen titration using the Microbix IgG ELISA", Product Technical Bulletin, URL://http://web.archive.org/web/2005 0526 2316 23/http://www.microbix.com/products/PDFs/TB-93-1AntigenTitraionousingtheMicrobixlgG+ELISA.pdf, 2005.
Mineva, I. et al., "Differential expression of alphaB-crystallin and Hsp27-1 in anaplastic thyroid carcinomas because of tumor-specific alphaB-crystallin gene (CRYAB) silencing", Cell Stress & Chaperones, Autumn 2005, 10(3):171-84.
Moingeon, "Strategies for designing vaccines eliciting Th1 responses in humans", Journal of Biotechnology, 2002, vol. 98, pp. 189-198.
Molina, et al., "Use of serial carcinoembryonic antigen and CA 15.3 assays in detecting relapses in breast cancer patients", Breast Cancer Res Treatr, 1995, 36:41-48.
Moll, R. et al., "The Catalog of Human Cytokeratins: Patterns of Expression in Normal Epithelia, Tumors and Cultured Cells", Cell, Nov. 31, 1982, 31(1), 11-24.
Montenarh, et al., "P53 Autoantibodies in the Sera, Cyst and Ascitic Fluids of Patients with Ovarian Cancer", International Journal of Oncology, 1998, vol. 13, 605-610.
Mudenda, et al., "The relationship between serum p53 autoantibodies and characteristics of human breast cancer", CR J Cancer, 1994, 69:4445-4449.
Munemitsu, S. et al., "Regulation of intracellular B-catenin levels by the adenomatous polyposis coli (APC) tumor-suppressor protein", PNAS, 1995, 92: 3046-50.
Munoz, et al., "New experimental criteria for optimization of solid-phase antigen concentration and stability in ELISA", J. Immunol. Methods, 1986, 20:137-44.
Muraki, et al., "Assessment of serum CYFRA 21-1 in lung cancer", Cancer, Apr. 1996, 77(7), 1274-7.
Muraki, M. et al., "Serum CYFRA 21-1 in Lung Cancer", Fourth Dept. of Internal Medicine, 1996, 1274-1277.
Narod, "Genetic epidemiology of prostate cancer", BBA-Reviews on Cancer, Jan. 1999, vol. 1423, No. 2, F1-F13.
Nery, "Isolation and Partial Characterization of Macromolecular Urinary Aggregates Containing Carcinoembryonic Antigen-Like Activity", Br. J. Cancer, 1974, vol. 29, No. 413.
Norum, L. F. et al., "Elevated CA 125 in Breast Cancer—A Sign of Advanced Disease", Tumour Biol., Jul.-Aug. 2001, 22(4), 223-8.
Nouwen, E. J. et al., "Occurrence of the mucinous differentiation antigen CA125 in genital tract and conductive airway epithelia of diverse mammalian species (rabbit, dog, monkey)", Differentiation, 1990, 45:192-198.
Nustad, et al., "Epitopes on CA 125 from Cervical Mucus and Ascites Fluid and Characterization of Six New Antibodies", Tumor Biol., 2002, 303-314.
Obiezu, C. V. et al., "Human tissue kallikrein gene family: applications in cancer", Cancer Lett., Jun. 2005, 224(1), 1-22.
O'Sullivan, et al., "Polymorphic epithelial mucin from the sera of advanced breast cancer patients—isolation and partial characterisation", British Journal of Cancer, 1990, vol. 61, pp. 801-808.
Pandha, et al., "Cellular and humoral responses to KRAS polynucleotide vaccines", Cancer Gene Therapy, 1997, vol. 4, No. 5, 310.
Pare, J. et al., "An enzyme-linked immunosorbent assay (ELISA) for serological diagnosis of *Neospora* sp. infection in cattle", Journal of Veterinary Diagnostic Investigation, 1995, AAVLD, Columbia MO, vol. 7, 352-359.
Pavelic, Z. et al., "Evaluation of c-myc proto-oncogene in primary human breast carcinomas", Anticancer Research, Jul.-Aug. 1991, 11(4):1421-1428.
Pedrero, J. M. G. et al., "Annexin A1 Down-Regulation in Head and Neck Cancer Is Associated with Epithelial Differentiation Status", American Journal of Pathology, 2004, 164(1), 73-79.
Perey, L., "Elevated CA125 levels in patients with metastatic breast carcinoma", Br J Cancer, Oct. 1990, 62(4), 668-670.
Petrakou, et al., "Preliminary Studies on the Binding of Human Autoantibodies to the MUC1 Antigen", International Journal of Oncology, 1997, vol. 11, Suppl., 902.
Petrarca, C. et al., "Human Antibodies Against the Polymorphic Epithelial Mucin in Ovarian Cancer Patients Recognise a Novel Sequence in the Tandem Repeat Region", European Journal of Cancer, 1996, vol. 32, No. 12, 2155-2163 (Abstract only).
Pratt, M. A. et al., "Estrogen activates raf-1 kinase and induces expression of EGR-1 in MCF-7 breast cancer cells", Mol Cell Biochem, Dec. 1998, 189(1-2), 119-25.
Prezas, P. "Overexpression of the human tissue kallikrein genes KLK4, 5, 6, and 7 increases the malignant phenotype of ovarian cancer cells", Biol. Chem., Jun. 2006, 387(6), 807-811.
Raghava, G. P. et al., "Method for determining the affinity of monoclonal antibody using non-competitive ELISA: A computer program", Journal of Immunoassay, 1994, 15(2), 115-128.
Rao, et al., "Detection of Human Ovarian Tumor Associated Antigens by Autologous Antibodies Isolated from Ovarian Carcinoma Ascites Fluid", Proceedings of the American Association of Cancer Research Annual Meeting, 1987, vol. 28 #1419, 358.
Rao, et al., "Detection of human ovarian tumor-associated antigens by antibodies isolated from ovarian carcinoma ascitic fluid", Am J Obstet Gynecol, Jul. 1998, vol. 159, 94-98.
Rasmussen, et al., "An ELISA for the detection of anti-neutrophil cytoplasm antibodies (ANCA)", J. Immunol. Methods, Feb. 1990, 127(1), 139-45 (Abstract only).
Reddish, M. A. et al., "Pre-immunotherapy serum CA27.29 (MUC-1) mucin level and CD69+ lymphocytes correlate with effects of Theratope siayl-Tn-KLH cancer vaccine in active specific immunotherapy", Cancer Immunol. Immunother, 1996, 42: 303-309.

(56) References Cited

OTHER PUBLICATIONS

Reiter, R. E. et al., "Prostate stem cell antigen: A cell surface marker overexpressed in prostate cancer", Proc Natl. Acad. Sci., 1998, 95:1735-1740.
Riddle, O. et al., "The preparation, identification and assey of prolactin—A hormone of the anterior pituitary", Am J. Physiol, 1933, 105(1), 191-216.
Robertson, et al., "Assessment of Four Monoclonal Antibodies as Serum Markers in Breast Cancer", Eur. J. Cancer, 1990, 26: 1127-1132.
Robertson, et al., "Prospective assessment of the role of five tumour markers in breast cancer", Cancer Immunol. Immunother., 1991, 33:403-410.
Robertson, et al., "Radioimmunohistochemistry of Epidermal Growth Factor Receptor in Breast Cancer", Archives of Pathology and Laboratory Medicine, 2001, 126:177-81.
Rosenberg, R. S. et al., "Modulation of Androgen and Progesterone Receptors by Phytochemicals in Breast Cancer Cell Lines", Biochem Biophys Res Commun., 1998, 248: 935-939.
Rughetti, et al., "Human B-Cell Immune Response to the Polymorphic Epithelial Mucin1", Cancer Research, Jun. 1, 1993, 53, pp. 2457-2459.
Rusciano, "Conomitant Purification of Prostatic Carcinoma Tumor Markers from Human Seminal Fluid Under Nondenaturing Conditions", Clinical Chemistry, 1988, vol. 34, No. 12, 2528-2532.
Sahin, et al., "Human neoplasms elicit multiple specific immune responses in the autologous host", PNAS, 1995, vol. 92, 11810-11813.
Sandrin, "Natural human anti-Gala(1,3)Gal antibodies react with human mucin peptides", Glycoconjugate Journal, 1997, 14:97-105.
Scanlan, et al., "Characterization of Human Colon Cancer Antigens Recognized by Autologous Antibodies", International Journal of Cancer, 1998, vol. 76, 652-658.
Schjetlein, Rune et al., "Choice of Standard Plasma for Diagnosis and Quantitation of Lupus Anticoagulants", Thrombosis Research, 1993, 72:287-294.
Schnieder, J., "P53 protein, EGF Receptor, and Anti-P53 Antibodies in Serum from Patients with Occupationally Derived Lung Cancer", British Journal of Cancer, 1999, vol. 80, No. 12, 1987-1994.
Scully, R. et al., "BRCA1 is a component of the RNA polymerase II holoenzyme", PNAS, 1997, 94: 5605-10.
Seabury, C. A. et al., "Evaluation of a new serum testing method for detection of prostate cancer", J Urol, Jul. 2002, 168(1):93-9.
Seitz, S. et al., "Genetic Background of Different Cancer Cell Lines Influences the Gene Set Involved in Chromosome 8 Mediated Breast Tumor Suppression", Genes Chromosomes Cancer, Jun. 2006, 45(6), 612-27.
Sharan, S. K. et al., "Embryonic lethality and radiation hypersensitivity mediated by Rad51 in mice lacking Brca2", Nature, 1997, 386: 804-810.
Shibata, et al., "Purification and Characterization of Prostate Specific Antigen from Human Urine", Biochimica et Biophysica Acta, 1997, vol. 1336, 425-433.
Sokoloff, et al., "A dual-Monoclonal Sandwich Assay for Prostate-Specific Membrane Antigen: Levels in Tissues, Seminal Fluid and Urine", The Prostate, 2000, vol. 43, 150-157.
Soussi, T., "The humoral response to the tumor-suppressor gene-product p53 in human cancer: implications for diagnosis and therapy", Immunology Today, Aug. 1996, Elsevier Publications, Cambridge GB, vol. 17, No. 8, 354-356.
Standker, et al., "Isolation and characterization of the circulating form of human endostatin", FEBS Letters, 1997, vol. 420, 129-133.
Stearns, et al., "Circulating tumor markers in breast cancer: Accepted utilities and novel prospects", Breast Cancer Research and Treatment, Abstract, Feb. 8, 1998, vol. 52, 239-259 (Abstract only).
Stedman, "Stedman's Medical Dictionary 27th Edition Definition of Fluid", http://www.thomsonhc.com/pdrel/librarian, 2004, Definitions of several words 1-3 accessed Dec. 17, 2007.
Stieber, et al., "A new marker in lung cancer", Cancer, Aug. 1993, 72(3), 707-13.
Stiller, D et al., "Immunohistochemical demonstration of alpha-fetoprotein in testicular germ cell tumors", Acta Histochem Suppl., 1986, Supp-Band 33:225-31.
Stockert, E. et al., "A Survey of the Humoral Immune Response of Cancer Patients to a Panel of Human Tumor Antigens", Journal of Experimental Medicine, 1998, 187 (8), 1349-1354.
Strnad, N. et al., "Simple determination of polysaccharide specific antibodies by means of chemically modified ELISA plates", Journal of Immunological Methods, Jun. 14, 1996, Elsevier Science Publishers B.V., vol. 193, No. 1, 1-7.
Stubbs, et al., "Faecal Carcinoembryonic Antigen (CEA) in patients with Large Bowel Cancer", European Journal of Surgical Oncology, 1987, vol. 13, 433-436.
Su, et al., "Association between Wild Type and Mutant APC Gene Products", Cancer Res., 1993, 53:2728-2731.
Szala, S. et al., "Molecular cloning of cDNA for the carcinoma-associated antigen GA733-2", Proc. Nat. Acad. Sci., 1990, 87:3542-3546.
Szekanecz, et al., "Increased production of the soluable tumor-associated Antigens CA19-9, CA125, andn CA15-3 in rheumatoid arthritis; potential adhesion molecules in synovial inflammation?", Ann. NY Acad Sci, Jun. 2007, 1108:359-371.
Tauchi, K. et al., "Expression of heat shock protein-70 and c-myc protein in human breast-cancer—an immunohistochemical study", Jap J Clin Oncol, 1991, 21(4), 256-63.
Taylor-Papadimitriou, "Report on the First International Workshop on Carcinoma-Associated Mucins", Int. J. Cancer, 1991, 49:1-5.
Thomas, W. M. et al., "Failure of CA19-9 to detect asymptomatic colorectal carcinoma", Br. J. Cancer, 1991, 63:975-976.
Tondini, et al., "Comparison of CA15-3 and Carcinoembryonic Antigen in Monitoring the Clinical Course of Patients with Metastatic Breast Cancer", Cancer Research, 1988, vol. 48, No. 14, 4107-4112.
Toth, et al., "A Carcinoembryonic Antigen (CEA) Binding Protein from Ascites Influnces CEA Uptake by Macrophages", Biochemical and Biophysical Research Communications, 1990, vol. 171, No. 2, 633-640.
Treon, et al., "Elevated soluble MUC1 levels and decreased anti-MUC1 antibody levels in patients with multiple myeloma", Blood, 2000, (96)6, pp. 3147-3153.
Tsai, et al., "Relationship of serum alpha-fetoprotein to circulating immune complexes and complements in patients with hepatitis B surface antigen-positive hepatocellular carcinoma", Gastroenterol Jpn, Jun. 1990, 25(3), 338-93.
Tsujimoto, Y. et al., "Analysis of the structure, transcripts, and protein products of Bcl-2, the gene involved in human follicular lymphoma", PNAS USA, 1986, 83(14), 5214-8.
Van Milligen, Florine J. et al., "Calculation of the affinity constant KASS for solid phase antigen: A model system using monoclonal antibodies against the cat allergen Fel d I", Journal of Immunological Methods, 1993, 162:165-173.
Vang, R. et al., "Cytokeratins 7 and 20 in Primary and Secondary Mucinous Tumors of the Ovary: Analysis of Coordinate Immunohistochemical Expression Profiles and Staining Distribution in 179 Cases", Am J. Surg Pathol, Sep. 2006, 30(9):1130-1139.
Venegas, et al., "Purification and Immunochemical Characterization of Ascitic Fluid Glycoproteins Containing Certain Tumor-Associated and Blood Group Antigen Markers", Glycoconjugate Journal, 1989, vol. 6, 551-524.
Voet, et al., Biochemistry, 1990, 1096 and 1098.
Voet, et al., Biochemistry, 1990, 78.
Voet, et al., Biochemistry, 1990, 78, 1096, 1098.
Volkmann, M. et al., "Anti-p53 autoantibodies as serological marker in different tumor-entities", Clinical Chemistry, Jul. 1995, vol. 41, No. S6 part 2, S221-S222.
Von Mensdorff-Pouilly, et al., "Circulating MUC1 Antibodies in Humans are Directed to More than One Region Within the MUC1 Mucin Peptide Core", Anticancer Research, Nov.-Dec. 1997, vol. 17, 4184.

(56) References Cited

OTHER PUBLICATIONS

Von Mensdorff-Pouilly, S , "Humoral Immune Response to Polymorphic Epithelial Mucin (MUC-1) inpatients with Benign and Malignant Breast Tumours", European Journal of Cancer, 1996, vol. 32A, No. 8, 1325-1331.
Warri, A. M. et al., "Anti-oestrogen Stimulation of ERBB2 Ectodomain Shedding from BT-474 Human Breast Cancer Cells with ERBB2 Gene Amplification", Eur. J. Cancer, 1996, 32A: 134-140.
Wolf, A. et al., "A Tumour-Associated Antigen from the Pleural Effusion of Patients with Squamous-Cell Carcinoma of Lung", Br. J. Cancer, 1978, vol. 36, 1046-1052.
Wolf, D. et al., "In Vitro Expression of Human p53 cDNA Clones and Characterization of the Cloned Human p53 Gene", Mol. Cell. Biol., 1985, 5(8):1887-1893.
Wolfe, et al., "A Tumour-Associated Antigen from the Pleural Effusion of Patients with Squamous-Cell Carcinoma of Lung", Br. J. Cancer, 1978, vol. 36, 1046-1052.
Wu, HY et al., "The expression of BIRC7 protein and mRNA in non-Hodgkin's lymphoma", Leukemia & Lymphoma, 2006, 47(6), 1110-6.
Xing, P. X. et al., "Phase I study of synthetic MUC1 peptides in breast cancer", Int. J. Oncol., 1995, 6(6): 1283-1289.
Xu, Z. et al., "Overexpression of Cox-2 in Human Osteosarcoma Cells Decreases Proliferation and Increases Apoptosis", C. Cancer Res., Jul. 1, 2006, 66(13), 3357-64.
Yamadori, et al., "A case of non-specific interstitial pneumonia associated with primary lung cancer: possible role of antibodies to lung cancer cells in the pathogenesis of non-specific interstitial pneumonia", Respiratory Medicine, 1999, 93, 754-756.
Yamamoto, et al., "Detection of auto-antibodies against c-Myc in sera from lung cancer patients", Proc. Amer. Soc. Cancer Res., Abstract, 1997, 564.
Yamamoto, et al., "L-Myc Overexpression and Detection of Auto-Antibodies Against L-Myc in both the Serum and Pleural Effusion from a Ptient with Non-Small Cell Lung Cancer", Internal Medicine, 1997, vol. 36, No. 10, 724-727.
Yamauchi, et al., "Autoantibodies to C-MYC Nuclear Protein Products in Autoimmune Disease", Immunology, Jan. 1990, 69(1):117-20.
Yang, D-K et al., "Development and evaluation of indirect ELISA for the detection of antibodies against Japanese encephalistis virus in swine", Journal of Veterinary Science, Sep. 30, 2006, vol. 7, No. 3, 271-275.
Yang, Y. C. et al., "Characterization of Genes Associated with Different Phenotypes of Human Bladder Cancer Cells", W. Acta Biochim Biophys Sin (Shanghai), Sep. 2006, 38(9), 601-10.
Yazici, H. et al., "Amplification in tumors and benign tissue of breast cancer patients", Cancer Lett., 1993, 107: 235-239.
Yousef, G. M. et al., "Expanded Human Tissue Kallikrein Family—A Novel Panel of Cancer Biomarkers", Tumor Biol, 2002, 23, 185-192.
Zehentner, B. K. et al., "Mammaglobin as a Novel Breast Cancer Biomarker: Multigene Reverse Transcription-PCR Assay and Sandwich ELISA", Clin Chem, Nov. 2004, 50(11), 2069-76.
Zehentner, B. K. et al., "Mammaglobin: a candidate diagnostic marker for breast cancer", Clin Biochem., Apr. 2004, 37(4), 249-57.
Zhang, J. et al., "Enhancement of Antibody Detection in Cancer Using Panel of Recombinant Tumor-associated Antigens", Cancer Epidemiology, Biomarkers & Prevention, 2003, vol. 12(2):136-143.
Zhu, Liyin et al., "Adenocarcinoma of Duodenum and Ampoulla of Vater: Clinicopathology Study and Expression of p53, c-neu, TGF-a, CEA, and EMA", Journal of Surgical Oncology, 1996, vol. 61; 100-105.
Zielen, et al., "Simple determination of polysaccharide specific antibodies by means of chemically modified ELISA plates", J. Immunol. Methods, Jun. 1996, 193(1), 1-7.
Zisman, et al., "Autoantibodies to Prostate Specific Antigen in Patients With Benign Prostatic Hyperplasia", Journal of Urology, 1995, vol. 154, 1052-1055.
U.S. Appl. No. 12/343,047, "Office Action" dated Apr. 5, 2012, 18.
U.S. Appl. No. 11/681,830 , "Non Final Office Action" dated Nov. 25, 2013, 10 pages.
U.S. Appl. No. 11/814,516 , "Notice of Allowance" dated Dec. 27, 2013, 10 pages.
U.S. Appl. No. 12/967,719 , "Non-Final Office Action" dated Oct. 18, 2013, 12 pages.
U.S. Appl. No. 13/438,344 , "Final Office Action" dated Dec. 16, 2013, 7 pages.
International Application No. PCT/GB2007/00346281 , "International Search Report" dated Dec. 19, 2007.
Takahashi et al., "Antibody to ras proteins in patients with colon cancer", Clin Cancer Res, vol. 1, 1995, p. 1071-1077.
Winter et al., "Development of Antibodies against p53 in Lung Cancer Patients Appears to Be Dependent on the Type of p53 Mutation", Cancer Res; vol. 52, 1992, p. 4168-4174.
U.S. Appl. No. 12/343,047 , "Non-Final Office Action", Feb. 27, 2014, 35 pages.
U.S. Appl. No. 14/035,092 , "Non-final office action", Jan. 15, 2014, 7 pages.
Opposition against European Patent No. 1 731 619 B1, filed Sep. 15, 2014.
Bayer and Wicheck, Immunochemical Applications of Avidin-Biotin Technology; Methods Mol Biol. 1992; 80: 149-62.
Cronan, Biotination of Proteins in Vivo A Post-Translational Modification to Label, Purify, and Study Proteins; Journal of Biol Chem. 1990; 265 (18): 10327-10333.
Franchimont et al., Simultaneous Assays of Cancer-Associated Antigens in Various Neoplastic Disorders; Cancer , 1976; 38(6): 2287-2295.
Zangerle et al., Casein and Other Tumor Markers in Relation to Cancer of the Breast, Antibiot Chemother 1971; 1978; 22: 141-8.

\* cited by examiner

FIG. 1
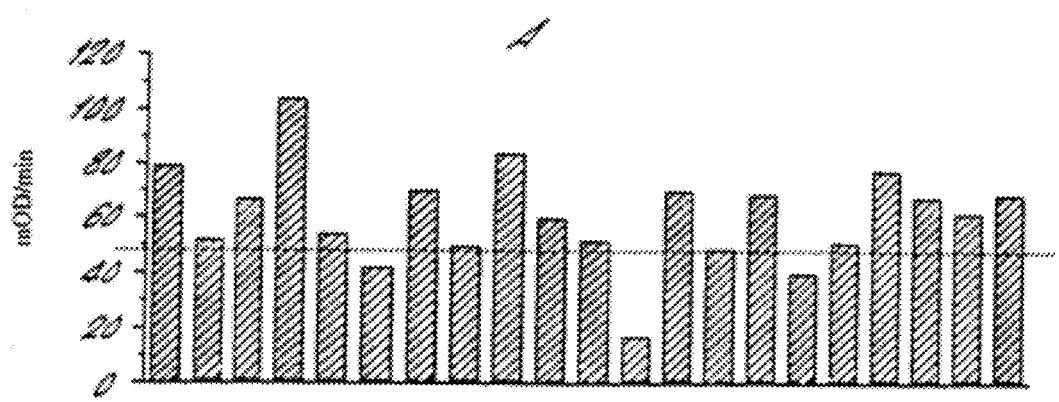
A
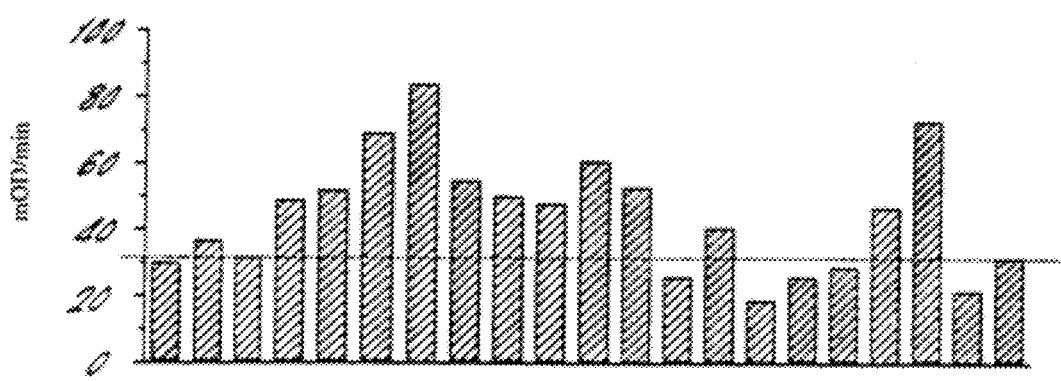
B
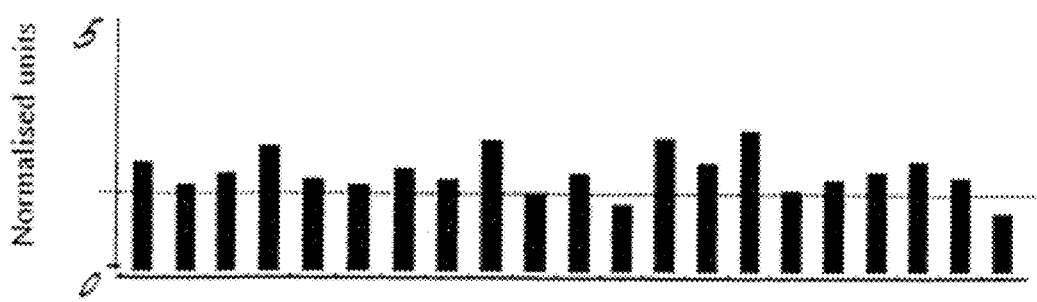
C

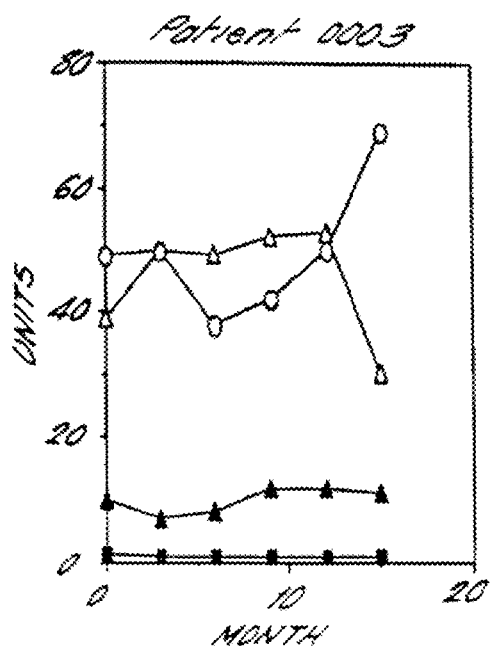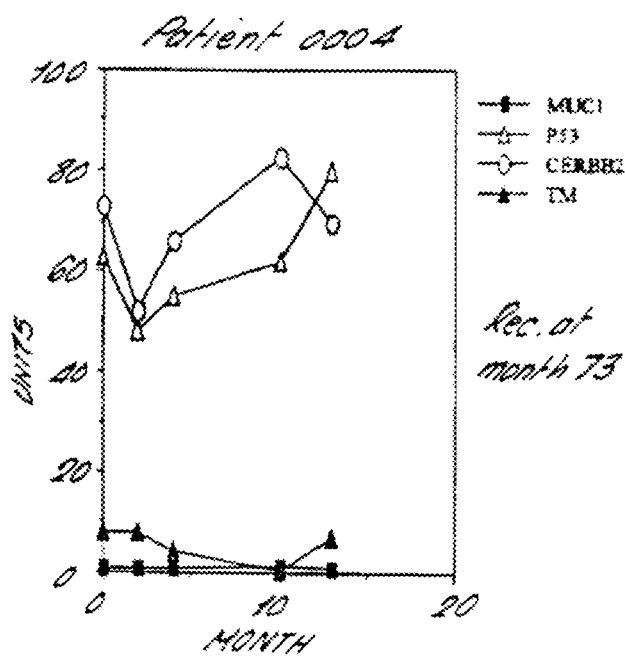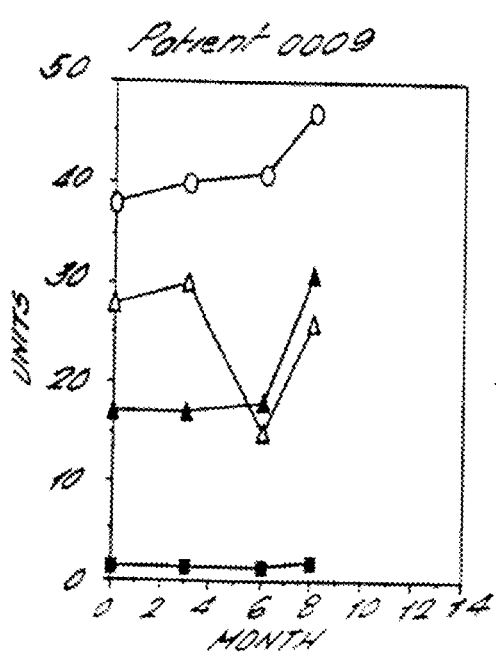
FIG. 3

TUMOUR MARKERS

CROSS REFERENCE TO RELATED APPLICATIONS

This application is a continuation application of U.S. patent application Ser. No. 11/953,237, which is a continuation application of U.S. patent application Ser. No. 09/700,092, filed May 16, 2001, which is a national stage filing under 35 U.S.C. §371 of PCT International Application PCT/GB99/01479, filed May 11, 1999, which claims priority to Great Britain Application No. 9810040.7, filed May 11, 1998, all of which are incorporated herein by reference.

The invention relates to methods of detecting or quantitatively measuring the immune response of a mammal to circulating tumour markers or tumour markers expressed on the surface of tumour cells, also to tumour marker antigens for use in these methods, to kits for performing the methods and to the use of these methods in the detection of cancer, in monitoring the progress of cancer, in detecting recurrent disease in cancer patients who have previously undergone anti-cancer treatment and in predicting the response of a cancer patient to a particular course of treatment.

The development and progression of cancer in a patient is generally found to be associated with the presence of markers in the bodily fluid of the patient, these "tumour markers" reflecting different aspects of the biology of the cancer (see Fateh-Maghadam, A. & Steilber, P. (1993) Sensible use of tumour markers. Published by Verlag GMBH, ISBN 3-926725-07-9). Tumour markers are often found to be altered forms of the wild type proteins expressed by 'normal' cells, in which case the alteration may be a change in primary amino acid sequence, a change in secondary, tertiary or quaternary structure or a change in post-translational modification, for example, abnormal glycosylation. Alternatively, wild type proteins which are up-regulated or over-expressed in tumour cells, possibly as a result of gene amplification or abnormal transcriptional regulation, may also be tumour markers.

Established assays for tumour markers present in bodily fluids tend to focus on the detection of tumour markers which reflect tumour bulk and as such are of value late in the disease process, for example, in the diagnosis of metastatic disease. The most widely used of these markers include carcinoembryonic antigen (CEA) and the glycoprotein termed CA 15.3, both of which have been useful mainly as indicators of systemic disease burden and of relapse following therapy (Molina, R., Zanon, G., Filella, X. et al. Use of serial carcinoembryonic antigen and CA 15.3 assays in detecting relapses in breast cancer patients. (1995) *Breast Cancer Res Treat* 36: 41-48) These markers are of limited use earlier in the disease progression, for example in the screening of asymptomatic patients. Thus, in the search for tumour markers present in bodily fluid that are of use earlier in the disease process the present inventors have sought to identify markers which do not depend on tumour bulk per se.

Differences between a wild type protein expressed by 'normal' cells and a corresponding tumour marker protein may, in some instances, lead to the tumour marker protein being recognised by an individual's immune system as 'non-self' and thus eliciting an immune response in that individual. This may be a humoral (i.e B cell-mediated) immune response leading to the production of autoantibodies immunologically specific to the tumour marker protein. Autoantibodies are naturally occurring antibodies directed to an antigen which an individual's immune system recognises as foreign even though that antigen actually originated in the individual. They may be present in the circulation as circulating free autoantibodies or in the form of circulating immune complexes consisting of autoantibodies bound to their target tumour marker protein.

As an alternative to the direct measurement or detection of tumour marker protein in bodily fluids, assays could be developed to measure the immune response of the individual to the presence of tumour marker protein in terms of autoantibody production. Such assays would essentially constitute indirect detection of the presence of tumour marker protein. Because of the nature of the immune response, it is likely that autoantibodies can be elicited by a very small amount of circulating tumour marker protein and indirect methods which rely on detecting the immune response to tumour markers will consequently be more sensitive than methods for the direct measurement of tumour markers in bodily fluids. Assay methods based on the detection of autoantibodies may therefore be of particular value early in the disease process and possibly also in relation to screening of asymptomatic patients, for example to identify individuals "at risk" of developing disease.

Tumour marker proteins observed to elicit serum autoantibodies include a particular class of mutant p53 protein, described in U.S. Pat. No. 5,652,115, which can be defined by its ability to bind to the 70 kd heat shock protein (hsp70). p53 autoantibodies can be detected in patients with a number of different benign and malignant conditions (described in U.S. Pat. No. 5,652,115) but are in each case present in only a subset of patients. For example, one study utilizing an ELISA assay for detection of autoantibodies directed against the p53 protein in the serum of breast cancer patients reported that p53 autoantibodies were produced by 26% of patients and 1.3% of control subjects (Mudenda, B., Green, J. A., Green, B. et al. The relationship between serum p53 autoantibodies and characteristics of human breast cancer. (1994) *Br J Cancer* 69: 4445-4449.). A second tumour marker protein known to elicit serum autoantibodies is the epithelial mucin MUC1 (Hinoda, Y. et al. (1993) Immunol Lett. 35: 163-168; Kotera, Y. et al. (1994) *Cancer Res.* 54: 2856-2860).

In most cancers resulting from a progressive accumulation of genetic alterations, such as breast cancer, the presence of tumour markers in bodily fluids reflects the development and progression of disease but no single marker on its own summates all clinically important parameters. For example, the characteristics of a marker useful for diagnosis of cancer may be quite different from markers which convey information about prognosis. Furthermore, in each clinical situation (i.e. diagnosis or prognosis) different markers may be required when dealing with primary cancer and secondary (metastatic) cancer and a different marker again may be required to provide a method of measuring the effectiveness of a particular course of treatment. Different clinical situations therefore require different biological markers and, as has been observed with p53, not all patients express the same set of tumour marker proteins. It is therefore difficult to envisage any one single tumour marker being universally applicable to all patients in all stages of disease.

It is an object of the present invention to provide an improved assay system for the detection of bodily fluids-borne tumour markers which is more generally useful in all patients and in a variety of different clinical situations.

Accordingly, in a first aspect the invention provides a method of detecting the immune response of a mammal to circulating tumour marker proteins or tumour cells expressing said tumour marker proteins, which method comprises steps of:

(a) contacting a sample of bodily fluids from said mammal with a panel of two or more distinct tumour marker antigens;
(b) determining the presence or absence of complexes of said tumour marker antigens bound to autoantibodies present in said sample of bodily fluids, said autoantibodies being immunologically specific to said tumour marker proteins.

whereby the presence of said complexes is indicative of the immune response to circulating tumour marker proteins or tumour cells expressing said tumour marker proteins.

The method of the invention, which may be hereinafter referred to as a 'panel assay', utilises a panel of two or more tumour marker antigens to monitor the overall immune response of an individual to a tumour or other carcinogenic/neoplastic change. The method thus provides essentially a 'profile' of the immune response for that individual, indicating which tumour markers elicit an immune response resulting in autoantibody production. The method of the invention is preferred for the detection of an immune response resulting in the production of circulating free autoantibodies.

Because the assay method of the invention performed on a sample of bodily fluids taken from the patient it is essentially non-invasive and can be repeated as often as is thought necessary to build up a profile of the patient's immune response throughout the course of disease. As used herein the term 'bodily fluids' includes plasma, serum, whole blood, urine, sweat, lymph, faeces, cerebrospinal fluid or nipple aspirate. The type of bodily fluid used may vary depending upon the type of cancer involved and the use that the assay is being put to. In general, it is preferred to perform the method on samples of serum or plasma.

As will be illustrated in the Examples given below, the use of a panel of two or more tumour marker antigens to monitor autoantibody production is more sensitive than the use of single markers and gives a much lower frequency of false negative results. The actual steps of detecting autoantibodies in a sample of bodily fluids may be performed in accordance with immunological assay techniques known per se in the art. Examples of suitable techniques include ELISA, radioimmunoassays and the like. In general terms, such assays use an antigen which may be immobilised on a solid support. A sample to be tested is brought into contact with the antigen and if autoantibodies specific to the tumour marker protein are present in the sample they will immunologically react with the antigen to form autoantibody-antigen complexes which may then be detected or quantitatively measured. Detection of autoantibody-antigen complexes is preferably carried out using a secondary anti-human immunoglobulin antibody, typically anti-IgG or anti-human IgM, which recognise general features common to all human IgGs or IgMs, respectively. The secondary antibody is usually conjugated to an enzyme such as, for example, horseradish peroxidase (HRP) so that detection of autoantibody/antigen/secondary antibody complexes is achieved by the addition of an enzyme substrate and subsequent colorimetric, chemiluminescent or fluorescent detection of the enzymatic reaction products.

The panel assay of the invention uses a panel of tumour marker-related antigens. The panel may be tailored to detect a particular cancer, or a cancer at a particular stage of development. The tumour marker antigens may be wild type or mutant tumour marker proteins isolated from samples of biological fluid from normal individuals or from cancer patients or from cell lines expressing the tumour marker protein or they may be full length recombinant tumour marker proteins, viral oncogenic forms of tumour marker proteins or antigenic fragments of any of the aforementioned proteins. The term 'antigenic fragment' as used herein means a fragment which is capable of eliciting an immune response.

The panel assay may be performed in a multi-well format in which each one of the two or more antigens is placed in a separate well of a multi-well assay plate or, alternatively, in a single-pot format in which the entire panel of antigens is placed in a single container. The panel assay may be performed in a qualitative format in which the objective is simply detection of the presence or absence of autoantibodies or in a quantitative format which provides a quantitative measurement of the amount of autoantibodies present in a sample.

Preferred markers for inclusion into the panel of tumour marker antigens include the epidermal growth factor receptor-related protein c-erbB2 (Dsouza, B. et al. (1993) *Oncogene*. 8: 1797-1806), the glycoprotein MUC1 (Batra, S. K. et al. (1992) *Int. J. Pancreatology*. 12: 271-283) and the signal transduction/cell cycle regulatory proteins Myc (Blackwood, E. M. et al. (1994) *Molecular Biology of the Cell* 5: 597-609), p53 (Matlashewski, G. et al. (1984) *EMBO J.* 3: 3257-3262; Wolf, D. et al. (1985) *Mel. Cell. Biol.* 5: 1887-1893) and ras (or Ras) (Capella, G. et al. (1991) *Environ Health Perspectives*. 93: 125-131), including the viral oncogenic forms of ras which can be used as antigens to detect anti-ras autoantibodies, and also BRCA1 (Scully, R. et al. (1997) *PNAS* 94: 5605-10), BRCA2 (Sharan, S. K. et al. (1997) *Nature*. 386: 804-810), APC (Su, L. K. et al. (1993) *Cancer Res*. 53: 2728-2731; Munemitsu, S. et al. (1995) *PNAS* 92: 3046-50), CA125 (Nouwen, E. J. et al. (1990) *Differentiation*. 45: 192-8) and PSA (Rosenberg, R. S. et al. (1998) *Biochem Biophys Res Commun*. 248: 935-939). As aforementioned, the assays can be formed using tumour marker antigens which are forms of these proteins isolated from human bodily fluids or from cultured cells or antigenic fragments thereof or full length or truncated recombinant proteins or antigenic fragments thereof.

Preferably the tumour marker antigens are labelled with biotin so that they can easily be attached to a solid support, such as a multi-well assay plate, by means of the biotin/avidin or biotin/streptavidin interaction. Tumour marker antigens labelled with biotin may be referred to herein as 'biotinylated' proteins. To facilitate the production of biotinylated tumour marker antigens for use in the assay methods of the invention, cDNAs encoding a full length recombinant tumour marker protein, a truncated version thereof or an antigenic fragment thereof may be expressed as a fusion protein labelled with a protein or polypeptide tag to which the biotin co-factor may be attached via an enzymatic reaction. A useful system for the expression of biotinylated fusion proteins is the PinPoint™ system supplied by Promega Corporation, Madison Wis., USA. The present inventors have surprisingly found that with the use of biotinylated tumour marker antigens as antigens they are able to detect autoantibodies in a much higher percentage of patients than is observed using non-biotinylated antigen.

The assay method of the invention may be employed in a variety of different clinical situations such as, for example, in the detection of primary or secondary (metastatic) cancer, in screening for early neoplastic or early carcinogenic change in asymptomatic patients or identification of individuals 'at risk' of developing cancer (particularly breast cancer, bladder cancer, colorectal cancer or prostate cancer) in a population or asymptomatic individuals, in the detection of recurrent disease in a patient previously diagnosed as carrying tumour cells who has undergone treatment to reduce the number of tumour cells or in predicting the response of an individual with cancer to a course of anti-cancer treatment.

The assay method of the invention is suitable for detection of many different types of cancer, of which examples are breast, bladder, colorectal, prostate and ovarian. The assay of the invention may complement existing methods of screening and surveillance. For example in the case of primary breast cancer it could be used to alert clinicians to biopsy small lesions on mammograms which radiographically do not appear suspicious or to carry out breast imaging or to repeat imaging earlier than planned. In the clinic, the assay method of the invention is expected to be more objective and reproducible compared to current imaging techniques (i.e. mammography and ultrasound), the success of which can be operator-dependent.

As aforesaid the panel of tumour marker antigens may be tailored having regard to the particular application. A panel of at least p53 and c-erbB2 is particularly useful for many types of cancer and can optionally be supplemented with other markers having a known association with the particular cancer, or a stage of the particular cancer, to be detected. For example for breast cancer the panel might include MUC 1 and/or c-myc and/or BRCA1 and/or BRCA2 and/or PSA whereas bladder cancer the panel might optionally include MUC 1 and/or c-myc, for colorectal cancer ras and/or APC, for prostate cancer PSA and/or BRCA1 or for ovarian cancer BRCA1 and/or CA125. There are other preferred embodiments in which p53 or c-erbB2 are not necessarily essential. For example, in the case of breast cancer suitable panels could be selected from the following:

p53 and MUC 1 with optional c-erbB2 and/or c-myc, and/or BRCA1 and/or BRCA2 and/or PSA;
p53 and c-myc with optional c-erbB2 and/or MUC1 and/or BRCA1 and/or BRCA2 and/or PSA;
p53 and BRCA1 with optional c-erB2 and/or MUC 1 and/or c-myc and/or BRCA2 and/or PSA;
p53 and BRCA2 with optional c-erbB2 and/or MUC 1 and/or c-myc and/or BRCA1 and/or PSA;
c-erbB2 and MUC 1 with optional p53 and/or c-myc, and/or BRCA1 and/or BRCA2 and/or PSA;
c-erbB2 and c-myc with optional p53 and/or MUC1 and/or BRCA1 and/or BRCA2 and/or PSA;
c-erbB2 and BRCA1 with optional p53 and/or MUC 1 and/or c-myc and/or BRCA2 and/or PSA;
c-erbB2 and BRCA2 with optional p53 and/or MUC 1 and/or c-myc and/or BRCA1 and/or PSA;

In the case of colorectal cancer suitable panels could be selected from the following:

p53 and ras with optional c-erbB2 and/or APC;
p53 and APC with optional c-erbB2 and/or Ras; Ras and APC with optional p53 and/or c-erbB2

In the case of prostate cancer suitable panels could be selected from the following:

p53 and PSA with optional BRCA1 and/or c-erbB2;
c-erbB2 and PSA with optional p53 and/or BRCA1.

In the case of ovarian cancer suitable panels could be selected from the following:

p53 and CA125 with optional c-erbB2 and/or BRCA1;
c-erbB2 and CA125 with optional p53 and/or BRCA1.

In a second aspect the invention provides a method of determining the immune response of a patient to two or more circulating tumour marker proteins or to tumour cells expressing said tumour marker proteins and identifying which one of said two or more tumour marker proteins elicits the strongest immune response in the patient, the method comprising contacting a sample of bodily fluids from said patient with a panel of two or more distinct tumour marker antigens, measuring the amount of complexes formed by binding of each of said tumour marker antigens to autoantibodies present in the sample of bodily fluids, said autoantibodies being immunologically specific to said tumour marker proteins and using the measurement obtained as an indicator of the relative strength of the immune response to each tumour marker protein and thereby identifying which one of said two or more tumour marker proteins elicits the strongest immune response in the patient.

The assay described above, which may be hereinafter referred to as a 'selection assay' is useful in the selection of a course of vaccine treatment wherein the single tumour marker protein identified as eliciting the strongest immune response or a combination of markers eliciting strong immune response is/are used as the basis of an anti-cancer vaccine treatment.

Preferred tumour marker antigens for use in the selection assay are any of the tumour marker antigens mentioned above and preferably the antigens are labelled with biotin. The actual steps of detecting autoantibodies in a sample of bodily fluids may be performed in accordance with known immunological assay techniques, as described above for the panel assay.

The invention also provides methods for the detection or quantitative measurement of the immune response of a mammal to a circulating tumour marker protein or tumour cells expressing the tumour marker protein wherein the tumour marker protein is MUC1, c-erbB2, Ras, c-myc, BRCA1, BRCA2, PSA, APC, CA125 or p53, the method comprising the steps of contacting a sample of bodily fluids from the mammal with the tumour marker antigen and determining the presence or absence of complexes of the tumour marker antigen bound to autoantibodies immunologically specific to the tumour marker protein or antigenic fragment thereof, whereby the presence of said complexes is indicative of the immune response to said circulating tumour marker protein or tumour cells expressing the tumour marker protein.

The assays described above, which may be hereinafter referred to as 'single marker assays', use a single type of tumour marker as antigen rather than using a panel of two or more tumour markers. The single marker assays may be used in any clinical situation, for example, screening for early neoplastic or carcinogenic change in asymptomatic patients, identification of individuals 'at risk' of developing cancer, early diagnosis and early detection of recurrence in a patient previously diagnosed as carrying tumour cells which patient has undergone treatment to reduce the number of said tumour cells or in predicting the response of a patient to a course of anti-cancer treatment, including surgery, radiotherapy, immune therapy, vaccination etc.

The single marker assays are particularly useful in situations where the tumour marker eliciting the strongest immune response in a given patient has been previously identified, possibly using the selection assay described above. For example, in a situation in which an initial selection assay has been performed to establish which tumour marker elicits the strongest immune response in a given patient, subsequent follow-up, detection of recurrence or monitoring of treatment may be carried out using a single marker assay to only detect or measure autoantibodies to that tumour marker previously identified as eliciting a strong immune response in that patient.

The actual steps of detecting autoantibodies in a sample of bodily fluids may be performed in accordance with known immunological assay techniques, as described above for the panel assay. Preferably the tumour marker protein used as antigen is labelled with biotin so that it may be easily attached to a solid support by means of the biotin/avidin or biotin/streptavidin interaction.

In a further aspect, the present invention provides a preparation comprising a human MUC1 protein which MUC1 protein manifests all the antigenic characteristics of a MUC1 protein obtainable from the bodily fluids of a patient with advanced breast cancer.

Preferably the MUC1 protein exhibits altered affinity for the antibodies B55, C595, BC4W154, DF3, B27.29, 115D8, 27.1, SM3, Ma552, HMPV and BC2 compared to MUC1 protein isolated from normal human urine. Most preferably the MUC1 protein is isolated from the serum of one or more human patients with advanced breast cancer. This can be accomplished using the protocol given in the Examples listed herein.

As will be described in detail in Example 2, the present inventors have found immunological differences between MUC1 isolated from normal individuals and MUC1 isolated from patients with advanced breast cancer. Possibly as a result of these differences, the inventors have found that the MUC1 protein isolated from serum of patients with advanced breast cancer (hereinafter referred to as ABC MUC1) is more sensitive when used as antigen in an assay to detect autoantibodies specific to MUC1 than either MUC1 isolated from urine of normal individuals, synthetic MUC1 or MUC1 isolated from a range of different cultured cells. MUC1 isolated from the serum of patients with advanced breast cancer is therefore preferred for use as antigen in the panel assay method and the single marker assay methods described herein.

MUC1 has recently attracted interest as a target for immunotherapy of adenocarcinomas and several Phase I clinical trials involving different MUC1 vaccine substrates, adjuvants and carrier proteins have been carried out (Goydos, J. S. et al. (1996) *J Surgical Res.* 63: 298-304; Xing, P. X. et al. (1995) *Int. J Oncol.* 6: 1283-1289; Reddish, M. A. et al. (1996) *Cancer Immunol. Immunother.* 42: 303-309; Graham, R. A. et al. (1996) *Cancer Immunol. Immunother.* 42: 71-80). Methods for the detection of anti-MUC1 autoantibodies using MUC1 isolated from the serum of patients with advanced breast cancer as antigen will be of particular use in monitoring the success of MUC1 vaccine therapy. In this case the aim of the assay will be to detect anti-MUC1 antibodies produced in response to the vaccine rather than autoantibodies i.e. antibodies produced in response to an exogenous antigen introduced into the body by vaccination. Methods for the detection of autoantibodies directed to other tumour markers would also be of use in monitoring the success of vaccine therapy using the relevant tumour marker. For example, following vaccination with a p53 antigenic preparation, the presence of anti-p53 antibodies could be monitored using the assay based on the use of biotinylated p53 antigen described in the examples given below. Moreover, the panel assay method could also be used in monitoring the success of vaccine therapy, for example, in a situation where an individual has been vaccinated with an antigenic preparation designed to elicit antibodies to two or more different tumour markers.

In a still further aspect the invention provides a method of detecting recurrent disease in a patient previously diagnosed as carrying tumour cells, which patient has undergone treatment to reduce the number of said tumour cells, which method comprises steps of contacting a sample of bodily fluids from the patient with MUC1 protein or an antigenic fragment thereof, determining the presence or absence of complexes of said MUC1 protein or antigenic fragment thereof bound to autoantibodies present in said sample of bodily fluids, said autoantibodies being immunologically specific to MUC1, whereby the presence of said complexes indicates the presence of recurrent disease in said patient.

The method described above may be repeated on a number of occasions to provide continued monitoring for recurrence of disease. The method is particularly preferred for the monitoring of patients previously diagnosed with primary breast cancer, colorectal cancer, prostate cancer or bladder cancer, which patients have undergone treatment (e.g. surgery) to remove or reduce the size of their tumour. In this instance, the presence of anti-MUC1 autoantibodies in the patient's serum after treatment may be indicative of recurrence of disease.

Also provided by the invention are assay kits suitable for performing the methods for the detection of autoantibodies described herein. Such kits include, at least, samples of the tumour marker antigens to be used as antigen in the assay and means for contacting the sample to be tested with a sample of the antigen.

The contents of all documents, articles and references cited herein are incorporated herein by reference.

The present invention will be further understood with reference to the following Examples and the accompanying Figures in which:

FIG. 1: shows the results of assays for autoantibodies to MUC1, p53 and c-erbB2 in samples of serum taken from 21 patients diagnosed with primary breast cancer. Panel A: anti-p53 autoantibodies; Panel B: anti-c-erbB2 autoantibodies and Panel C: anti-MUC1 autoantibodies. In each case, the dotted line represents the cut-off value for normality.

FIG. 2: shows reactivity profiles of MUC1 protein isolated from normal human urine (panel A), ABC MUC1 isolated from the serum of patients with advanced breast cancer (panel B) or MUC1 isolated from the human breast cancer cell line ZR75-1 (panel C) with various monoclonal anti-MUC1 antibodies.

FIG. 3: shows continuous monitoring for recurrent disease in three post-operative breast cancer patients. Quantitative assays for anti-MUC1, anti-cerbB2 and anti-p53 autoantibodies and for the tumour marker CA15-3 (™) were performed on samples of serum taken at two or three monthly intervals post-surgery.

Figure 4:
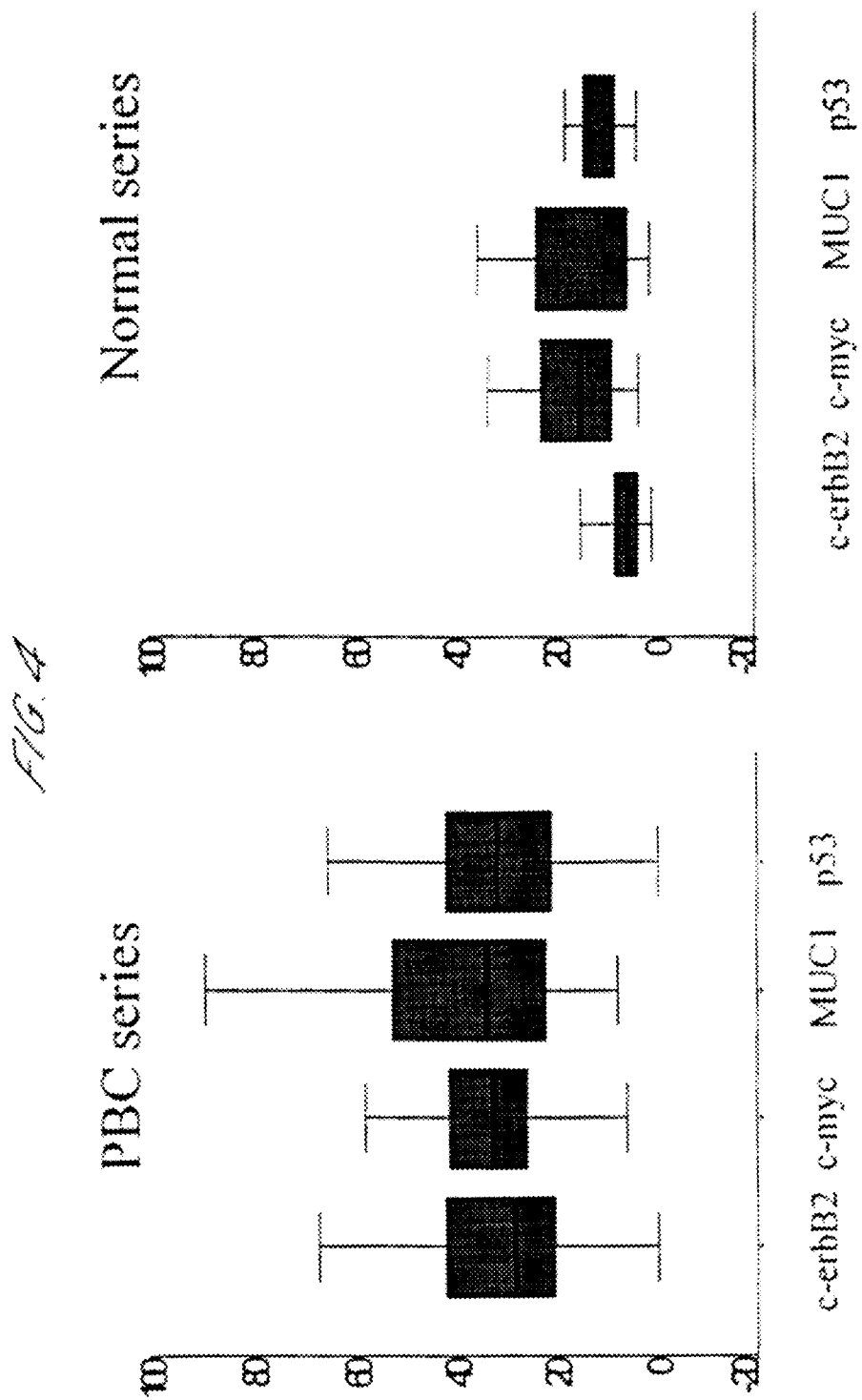

FIG. 4: shows the range of autoantibody levels found in assays for autoantibodies to c-erbB2, c-myc, MUC1 and p53 in normal individuals and patients with early primary breast cancer (PBC).

Figure 5:

FIG. 5: summarises the detection rate for primary breast cancer in an analysis of autoantibody levels in a series of healthy controls and patients with primary breast cancer, PBC subdivided by Stage 1—i.e. lymph node negative and Stage 2—i.e. lymph node positive and patients with metastatic cancer at 100% confidence.

Figure 6:
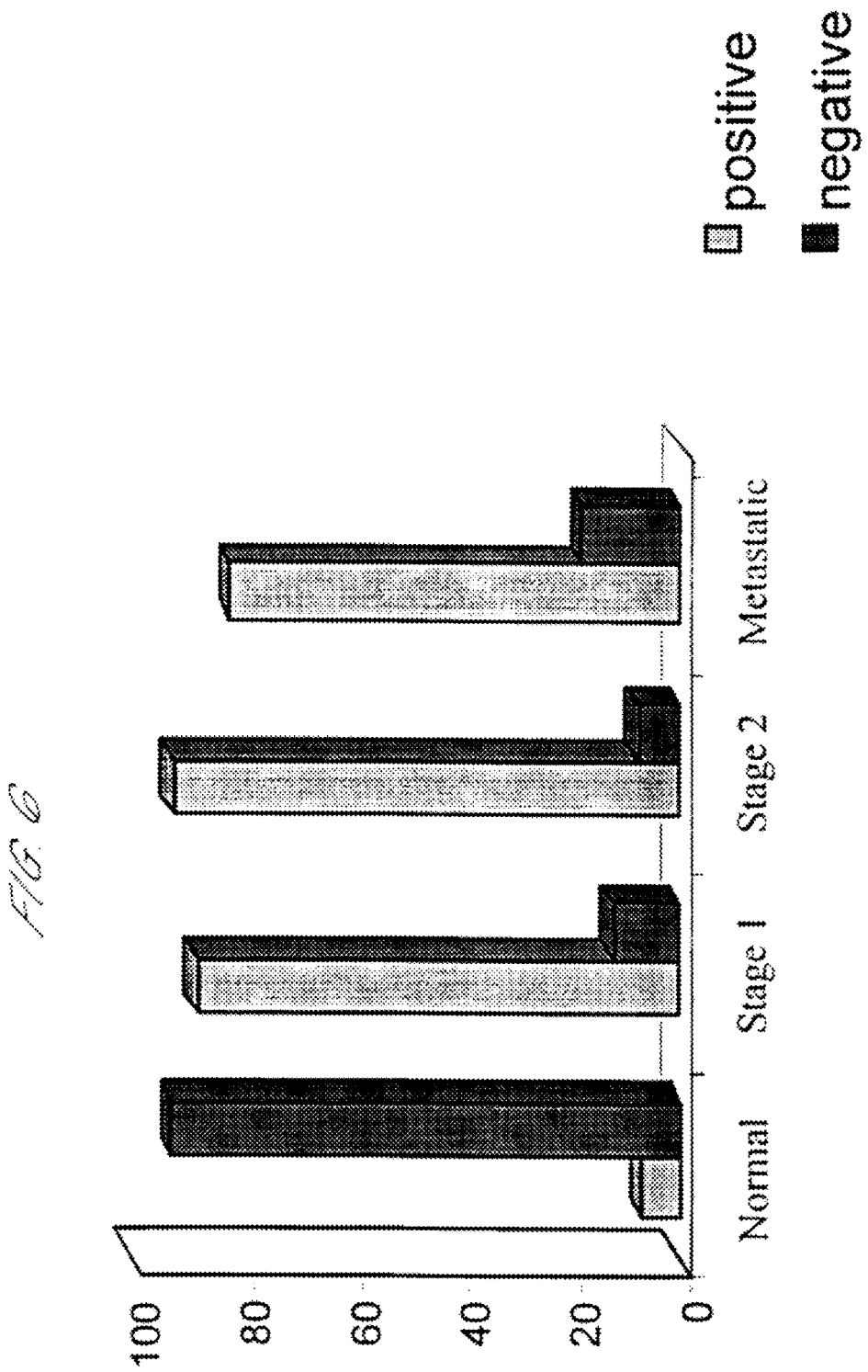

FIG. 6: summarises the detection rate for primary breast cancer in an analysis of autoantibody levels in a series of healthy controls and patients with PBC subdivided by Stage 1—i.e. lymph node negative and Stage 2—i.e. lymph node positive and patients with metastatic cancer at 95% confidence.

Figure 7:
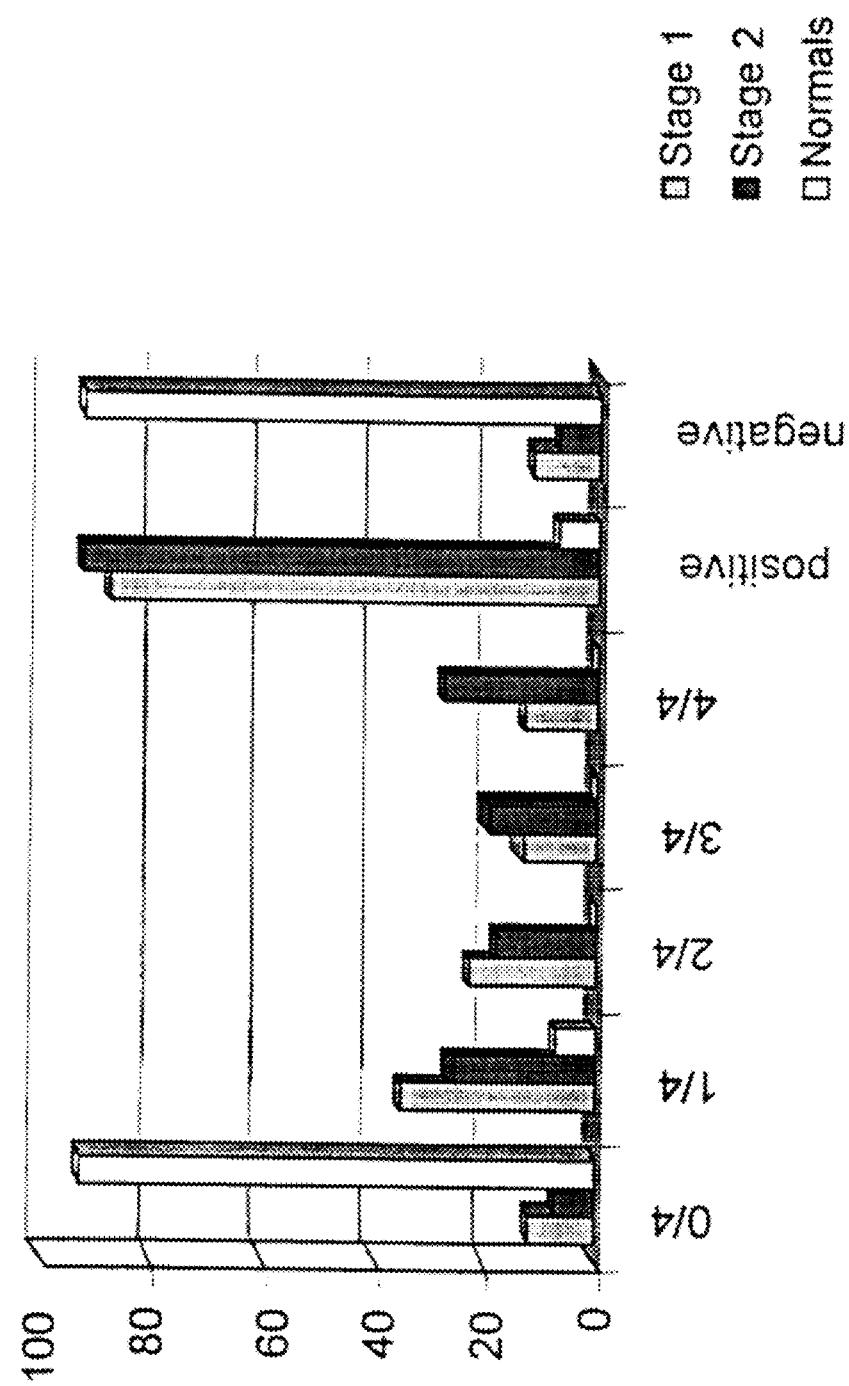

FIG. 7: shows the sensitivity for primary breast cancer in an analysis of autoantibody levels in a series of healthy controls and patients with Stage 1 or Stage 2 primary breast cancer at 95% confidence.

Figure 8:
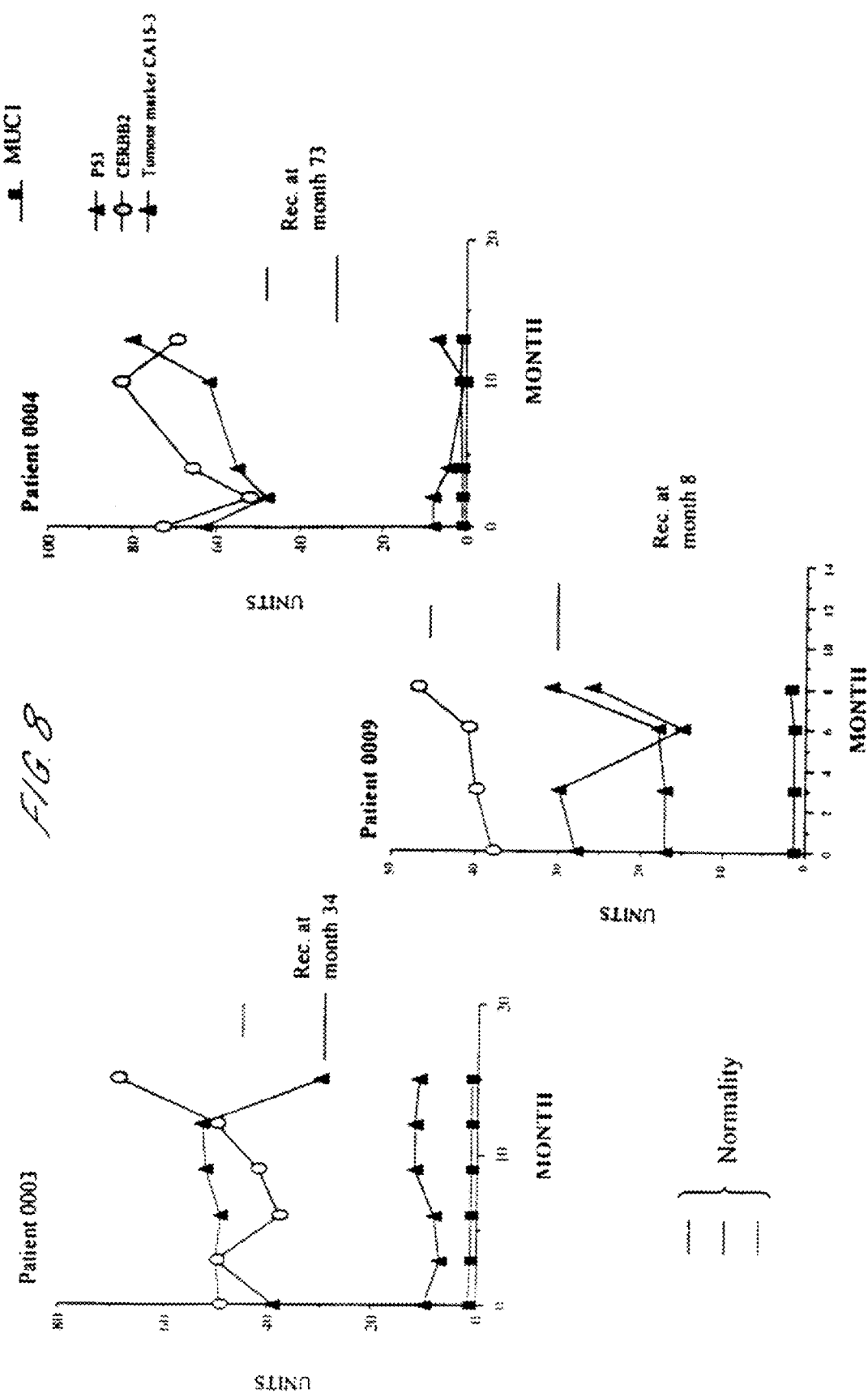

FIG. 8: shows the levels of autoantibodies to MUC1, p53 and c-erbB2 in the serum of three patients previously diagnosed with breast cancer measured sequentially during follow-up until the patient manifested recurrent disease.

Figure 9:
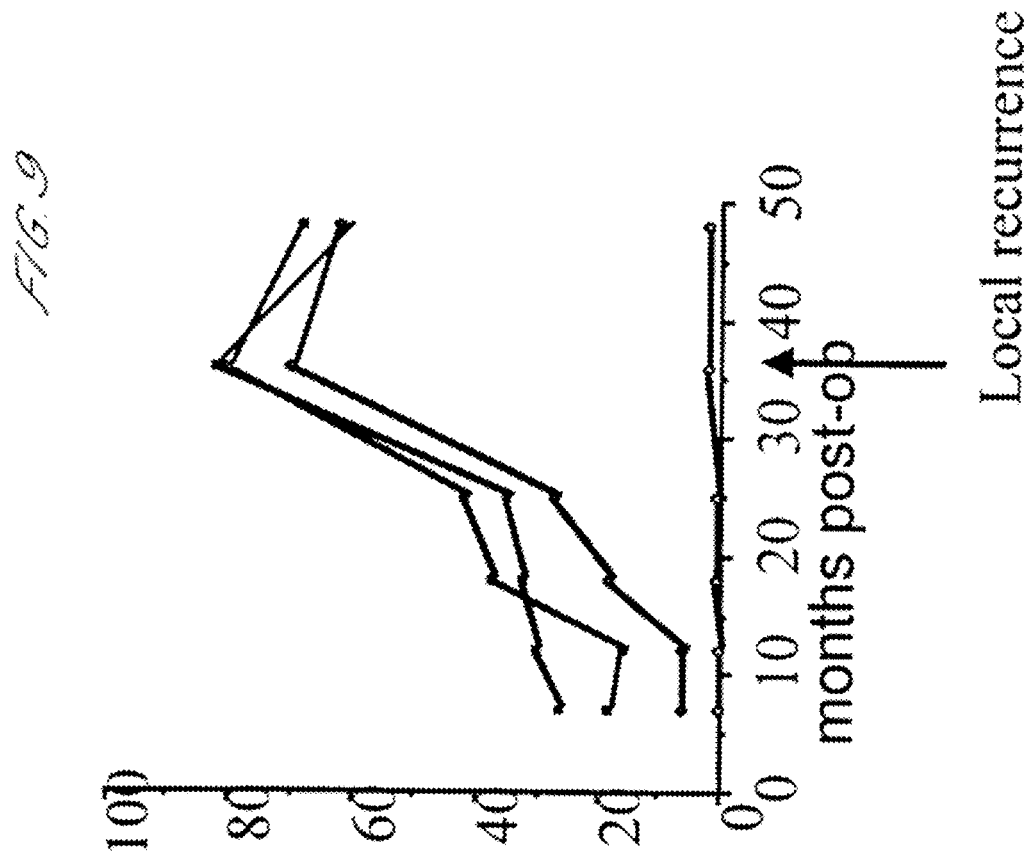
Figure 10:
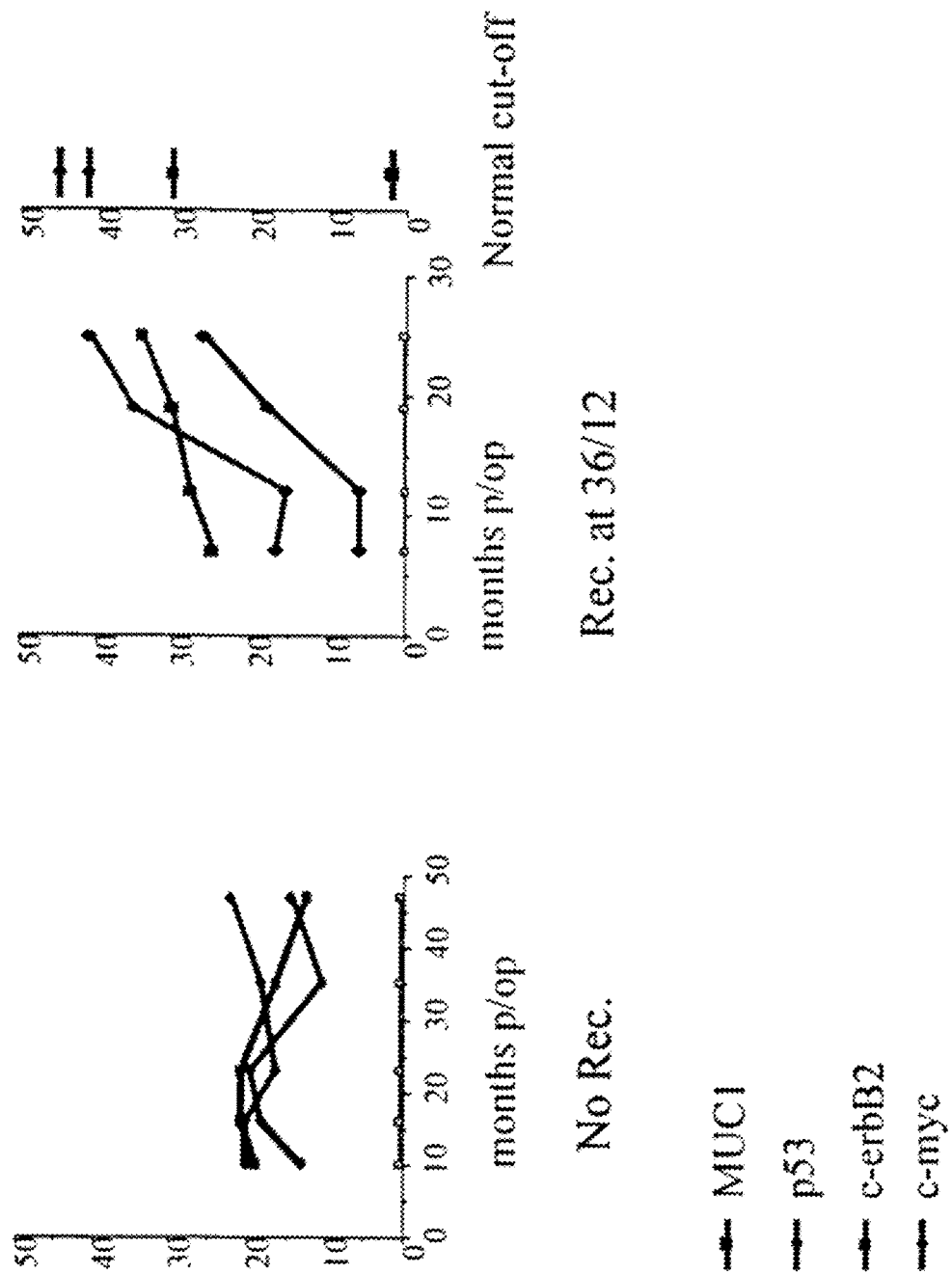

FIG. 9: shows the autoantibody levels in further samples from the second patient in FIG. 10 (AEC at 36 months) taken up to recurrence and during treatment for recurrence. Sequential measurements of established tumour markers reflecting tumour bulk (e.g. CA15-3 and CEA) were within the normal range throughout this period (data not shown).

FIG. 10: shows follow-up autoantibody levels in post-operative serum samples from two patients, one who did not develop recurrent disease (no REC) and the other who did (REC at 36 months).

Figure 11:
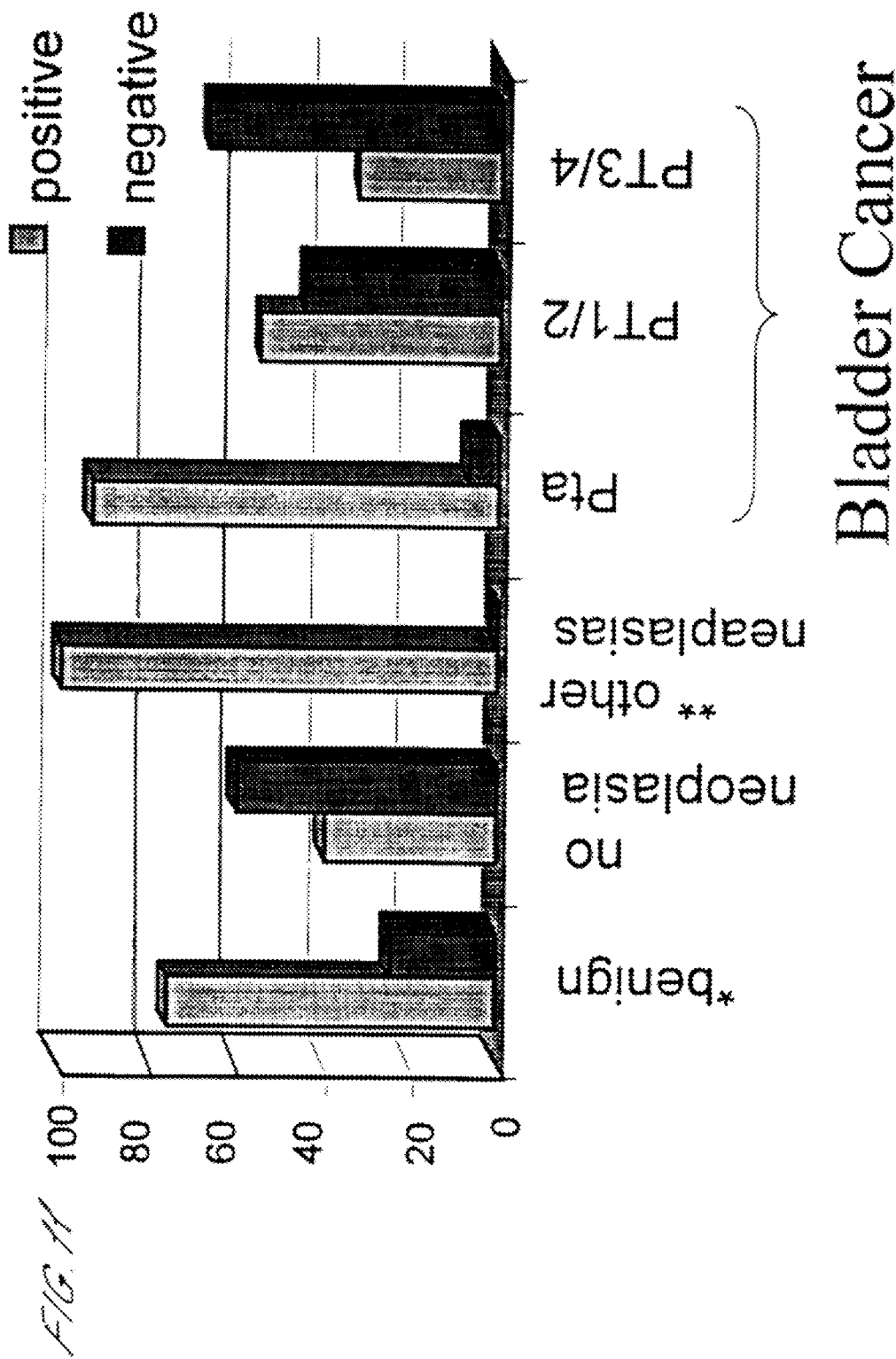

FIG. 11: summarises the detection rates in an analysis of autoantibody levels (p53, MUC1, c-erbB2 and c-myc) in samples of serum taken from patients with urologically benign disorders and various stages of bladder cancer.

\* indicates patients which were benign with respect to urology (i.e. did not have a urological malignancy), but six cases (all with positive autoantibody status) had evidence of other malignancies.

\*\* Other malignancies were: —lung cancer, skin cancer, adenocarcinoma of unknown primary. Evidence of other neoplasia consisted of: —pleural effusion, ovarian cysts, colon polyps.

Figure 12:
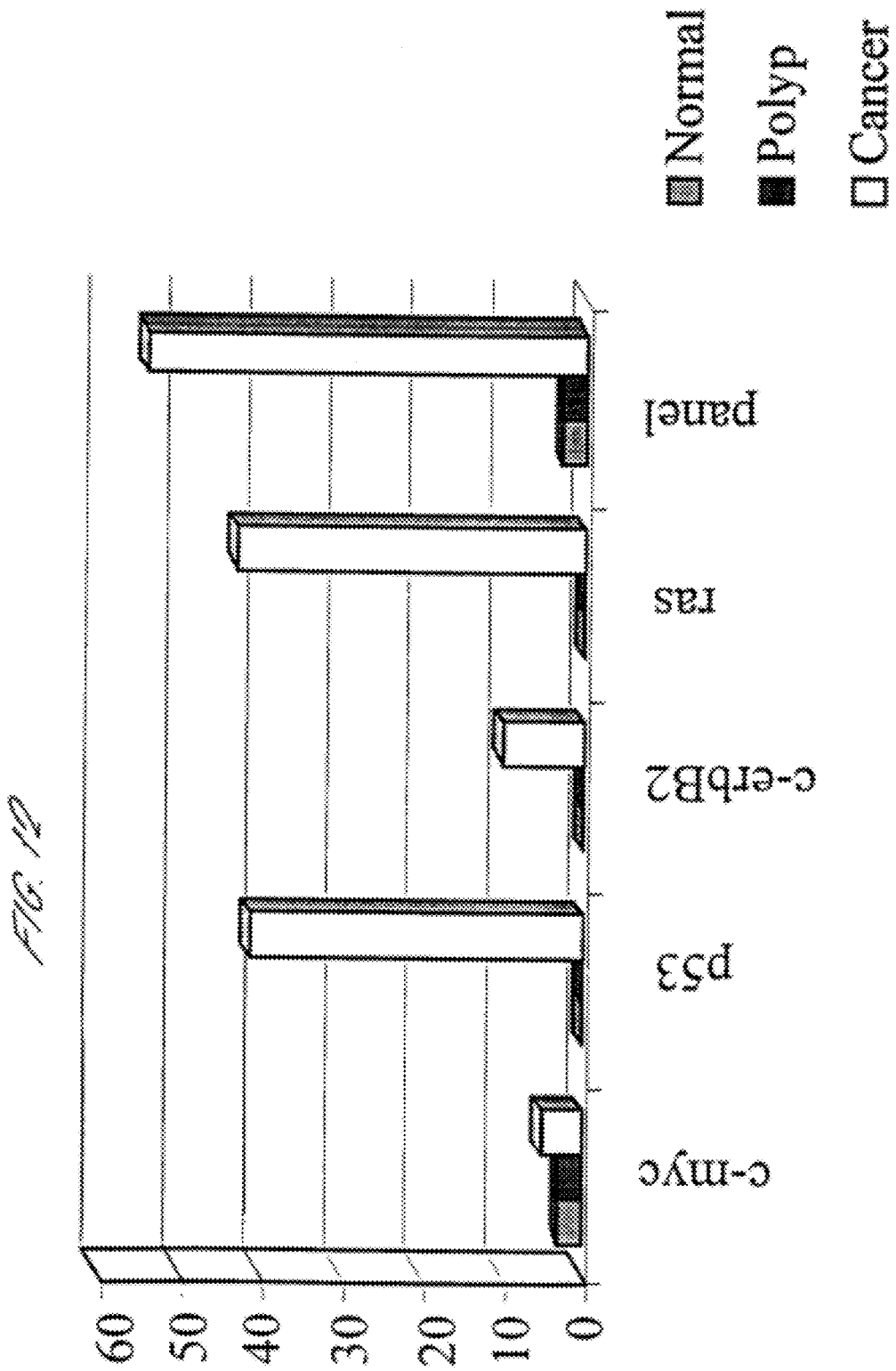

FIG. 12: summarises the detection rate for colorectal cancer in an analysis of autoantibody levels in the serum of healthy controls, patients with colonic polyps and patients with colorectal cancer at 100% confidence compared to a pre-defined group of healthy controls.

Figure 13:
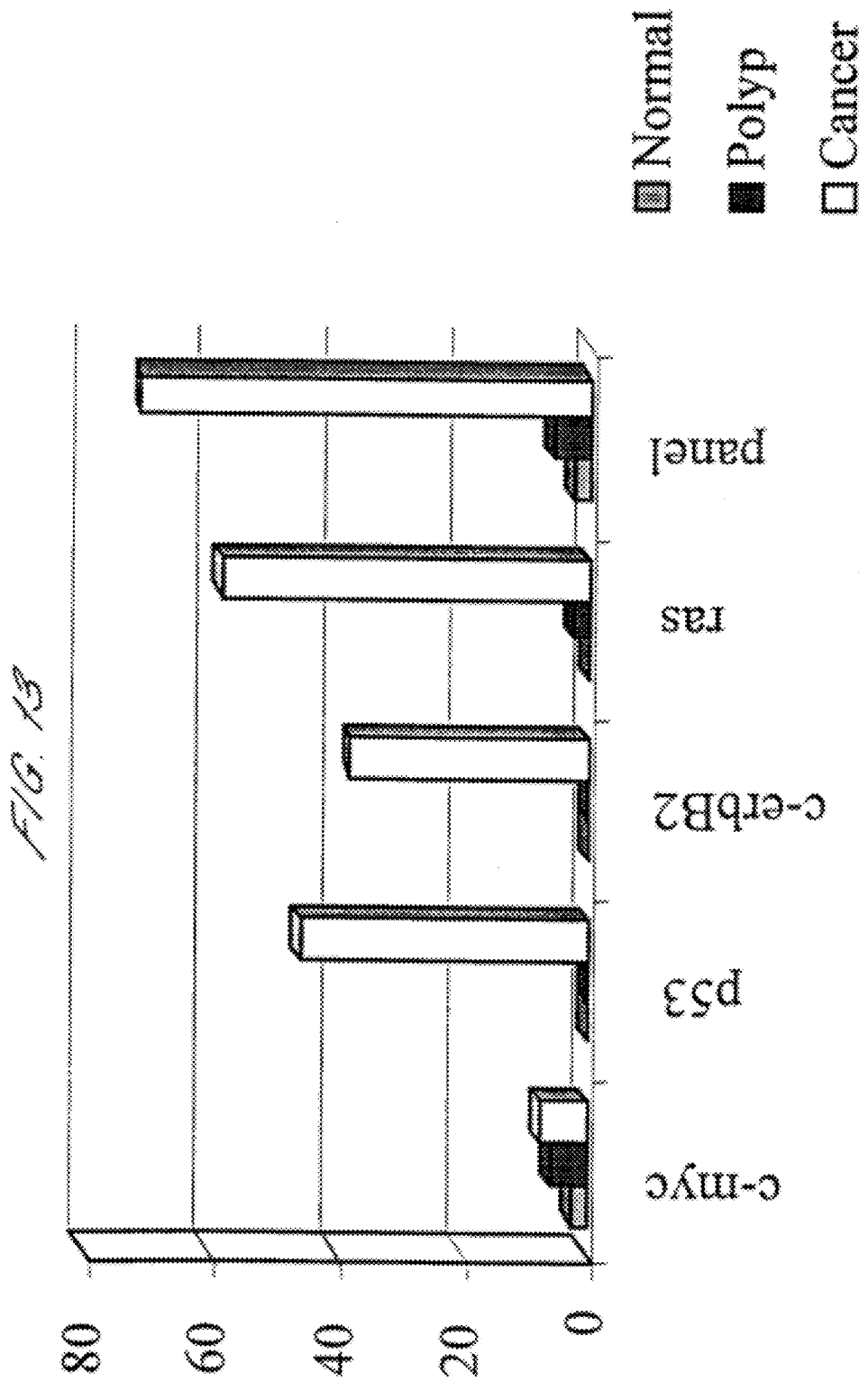

FIG. 13: summarises the detection rate for colorectal cancer in an analysis of autoantibody levels serum of healthy controls, patients with colonic polyps and patients with colorectal cancer at 95% confidence compared to a pre-defined group of healthy controls.

Figure 14:
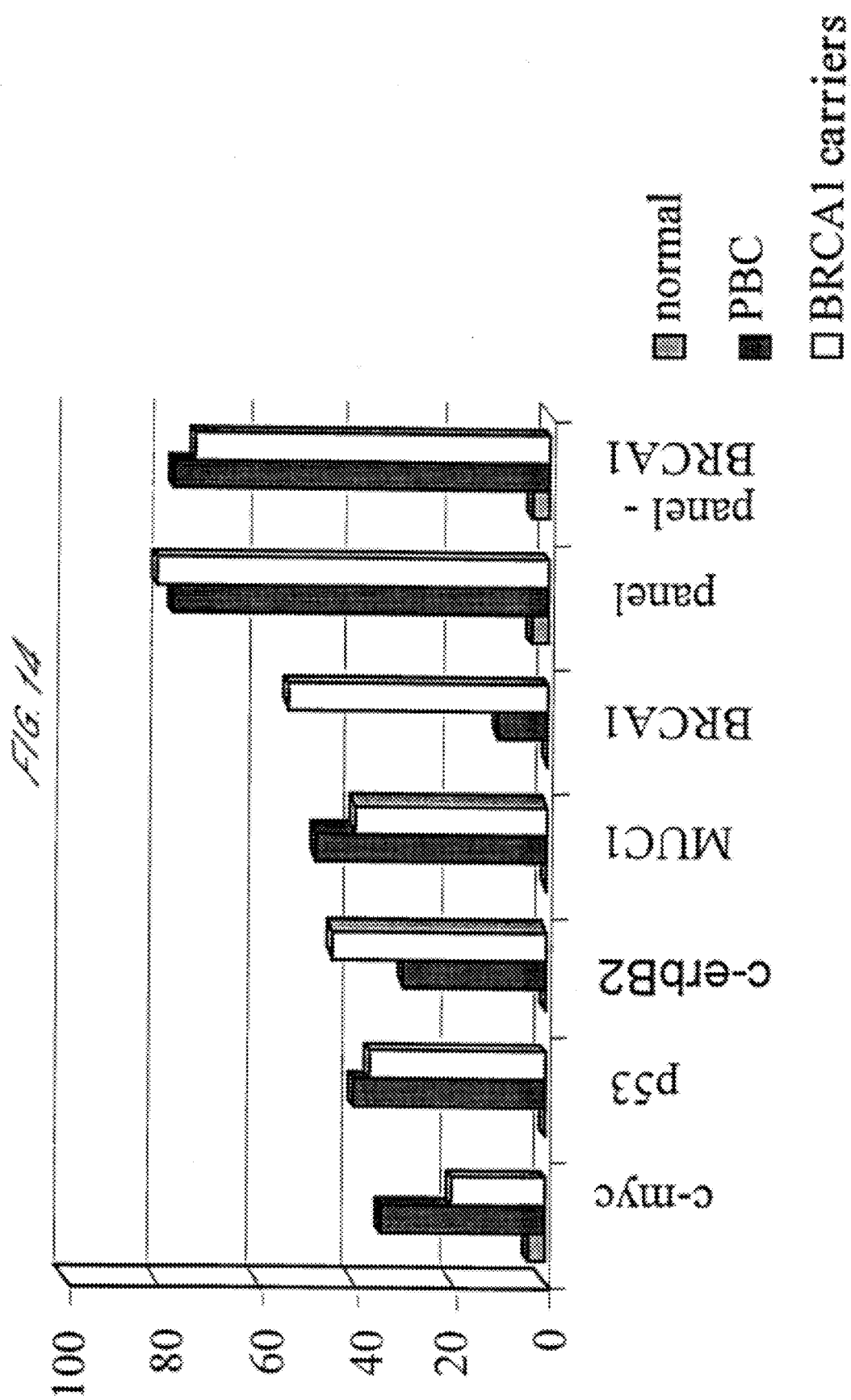

FIG. 14: summarises the detection rate in an analysis of autoantibody levels in the serum of healthy controls, patients with primary breast cancer and asymptomatic women known to be BRCA1 mutant carriers at 100% confidence compared to a pre-defined group of healthy controls.

Figure 15:
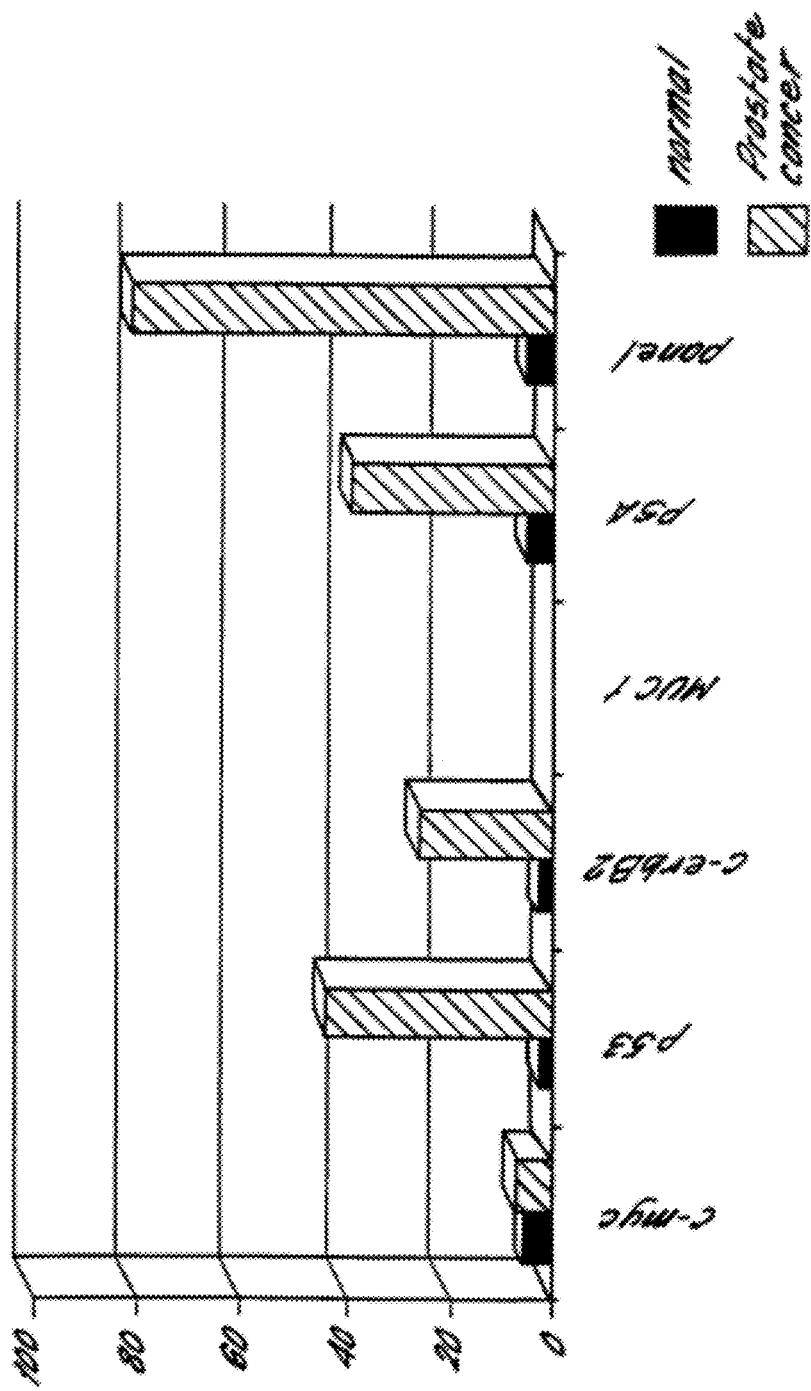

FIG. 15: summarises the detection rate for prostate cancer in an analysis of autoantibody levels in the serum of healthy controls and patients with prostate cancer at 95% confidence compared to a pre-defined group of healthy controls.

EXAMPLES

Example 1

Isolation of ABC MUC1 from Advanced Breast Cancer Patients

Method

ABC MUC1 was purified from pooled sera taken from 20 patients with advanced breast cancer using immunoaffinity chromatography as follows:

The mouse monoclonal anti-MUC1 antibody B55 (also known as NCRC 11 and described by Ellis et al. (1984) *Histopathology*. 8: 501-516 and in International patent application No. WO 89/01153) was conjugated to CNBrsepharose beads. Pooled sera from patients diagnosed with advanced breast cancer was diluted 1/10 in phosphate buffered saline (PBS) and then incubated with the antibody conjugated sepharose beads (25 ml diluted sera to 1 ml packed volume of beads) overnight at 4° C. with rolling. The beads were then packed by centrifugation and the supernatant removed. In order to wash away unbound serum components the beads were resuspended in PBS, rolled for 10 minutes, packed by centrifugation and the supernatant removed. This washing sequence was repeated 5 times (or until A280 nm of the supernatant was ~0). The washed beads were then resuspended in 0.25M glycine pH 2.5, rolled at room temperature for 10 minutes, packed by centrifugation and the supernatant removed. This supernatant was adjusted to pH 7 by the addition of Tris and stored at 4° C. labelled 'glycine fraction'. The beads were then resuspended in 1 ml 25 mM diethylamine (DEA) pH11, rolled at room temperature for 10 minutes, packed by centrifugation and the supernatant removed. This supernatant was again adjusted to pH 7 by the addition of Tris and stored at 4° C. labelled '25 DEA fraction'. The beads were finally resuspended in 1 ml 100 mM DEA pH11, rolled at room temperature for 10 minutes, packed by centrifugation and the supernatant removed. The final supernatant was again adjusted to pH 7 by the addition of Tris and stored at 4° C. labelled '100 DEA fraction'. The MUC1 content of the three fractions (glycine fraction, 25 DEA fraction and 100 DEA fraction) was confirmed by ELISA using the mouse monoclonal anti-MUC1 antibody C595 (commercially available from Serotec).

Example 2

Immunological Characterisation of ABC MUC1 Isolated from the Serum of Patients with Advanced Breast Cancer ABC MUC1 isolated from the serum at least 20 patients with advanced breast cancer according to the procedure described in Example 1 can be distinguished from MUC1 isolated from the urine of normal human subjects (normal human urinary MUC1) on the basis of altered affinity for the following mouse monoclonal anti-MUC1 antibodies:

| | |
|---|---|
| B55 (NCRC 11) | |
| C595 | |
| BC4W154 | Obtainable from Hybritech, Inc |
| DF3 | Obtainable from Centocor |
| B27.29 | Obtainable from Biomira, Inc |
| 115D8 | Obtainable from Centocor |
| 27.1 | Obtainable from Austin Research Institute |
| SM3 | Obtainable from the Imperial Cancer Research Fund |
| Ma552 | Obtainable from CanAg |
| HMPV | Obtainable from Austin Research Institute |
| BC2 | Obtainable from Austin Research Institute |

Normal urinary MUC1 is available from Dr M. R. Price, Cancer Research Laboratories, The University of Nottingham, University Park, Nottingham. NG7 2RD, United Kingdom.

The affinity of each of the above antibodies for ABC MUC1, normal human urinary MUC1 and also MUC1 protein purified from the human breast cancer cell line ZR75-1 (purified from a tissue culture supernatant by gel filtration) was measured by performing colorimetric ELISA assays using each of the different antibodies and secondary anti-immunoglobulin antibodies conjugated to HRP. Following addition of the colorimetric substrate (TMB), measurements were taken of OD at 650 nm. The results of the ELISA assays are presented graphically in FIG. 2. Values of Kd for the binding of several of these antibodies to ABC MUC1 and normal human urinary MUC1 are summarised in Table 1:

TABLE 1

Kd values for binding of monoclonal antibodies
to ABC MUC1 and normal human urinary MUC1.

| Monoclonal | Kd vs ABC MUC1 | Kd vs urinary MUGS |
|---|---|---|
| BC4W154 | $2.4 \times 10^{-7}$ | $1.7 \times 10^{-9}$ |
| 115D8 | $1 \times 10^{-8}$ | $3.38 \times 10^{-8}$ |
| C595 | $2.4 \times 10^{-8}$ | $2.5 \times 10^{-8}$ |

Example 3

Cloning of Biotinylated p53

Method

Commercially available cDNA for p53 (*E. coli* clone pBH53, deposited in the American Type Culture Collection under accession number 79110) was cloned into the PinPoint™ plasmid vector (Promega Corporation, Madison Wis., USA) using standard molecular biology techniques. The PinPoint™ vector is designed to facilitate the production of fusion proteins comprising a biotinylation domain (consisting of a fragment of a biotin carboxylase carrier protein) fused N-terminally to the target protein of interest. Care was therefore taken during the cloning procedure to ensure that the reading frame of p53 was maintained in the fusion protein. Procedures for cloning in PinPoint™ vectors are described in detail in the Promega Protocols and Applications Guide obtainable from Promega Corporation, Madison Wis., USA.

Fusion proteins expressed from the PinPoint™ vector in *E. coli* are biotinylated by an enzyme system of the *E. coli* host cells and may therefore be purified or bound to an assay plate using conventional avidin or streptavidin technology. For example, procedures for purification of the fusion protein using avidin covalently attached to a polymethacrylate resin are described in the Promega Protocols and Applications Guide obtainable from Promega Corporation, Madison Wis., USA.

Example 4

Cloning of c-erbB2

Method

Full-length cDNA encoding c-erbB2 was cloned from the human breast cancer cell line ZR75-1, which can be induced to up-regulate c-erbB2 expression by treatment with the anti-cancer drug tamoxifen.

Two T25 flasks of sub-confluent ZR75-1 cells (available from the American Type Culture Collection and from the European Collection of Cell Cultures, deposit number ATCC CRL1500) grown in RPMI plus 10% foetal calf serum were induced to express c-erbB2 by 4 day stimulation with tamoxifen at 7.5 pM (see Warri et al. (1996) *Eur. J. Cancer.* 32A: 134-140). The cells were then harvested using trypsin/EDTA and washed three times with PBS.

mRNA was extracted from the cell pellet using a Dynabead mRNA purification kit according to the manufacturer's recommended protocol. The mRNA was then used as a template for first strand cDNA synthesis using the Pharmacia Ready-to-go™ T primed first strand cDNA synthesis kit. cDNA/mRNA was then blunt end ligated into the EcoRV site of the PinPoint™ vector. The ligation products were then transformed into Top 10 F *E. coli* cells (Invitrogen) following the manufacturer's supplied protocol and the transformed cells grown overnight on LB agar plates containing ampicillin. Colonies of the transformed *E. coli* were copied onto nitrocellulose filter and then grown for 2 hours on LB agar containing ampicillin and IPTG (1 mM). The colonies on the nitrocellulose filter were fixed and lysed (15 minutes in the presence of chloroform vapour followed by 18 hours in 100 mM Tris/HCL pH 7.8; 150 mM NaCl; 5 mM MgC12; 1.5% BSA; 1 µg/ml DNase 1; 40 µg/ml lysozyme).

Screening for colonies expressing anti-c-erbB2 reactive protein was carried out as follows:
1. Wash nitrocellulose filter three times in TNT (10 mM Tris/HCl pH 8; 150 mM NaCl; 0.05% Tween 20) then block for 60 minutes in TNT+5% dried milk protein.
2. Incubate nitrocellulose filter for 2 hours at room temperature with mouse anti-c-erbB2 antibody (Ab-3 from Oncogene Research Products, Calbiochem).
3. Wash the filter three times in TNT then incubate overnight at 4° C. with anti-mouse HRP conjugate.
4. Wash filter three times in TNT, twice in TN (10 mM Tris/HCl pH 8; 150 mM NaCl) then visualise colonies expressing anti-c-erbB2 reactive protein using chloronaphthol (6 mg chloronaphthol in TN+6 µl 30% $H_2O_2$).
5. After development (approximately 20 minutes treatment with chloronaphthol as described in step 4) wash filter with water and allow to air dry.

Colonies identified as positive for c-erbB2 expression were picked and grown up overnight in liquid culture of LB+ampicillin and small amounts of plasmid DNA and protein were prepared from the culture for analysis. Plasmids containing a c-erbB2 cDNA insert were identified using restriction enzyme digestion and PCR using a primer pair specific to the published c-erbB2 cDNA sequence, described by Yazici, H. et al. (1996) *Cancer Lett.* 107: 235-239. DNA sequence analysis could then be used to confirm 1) the presence of a c-erbB2 insert and 2) that the reading frame of c-erbB2 is maintained in the resultant biotinylated fusion protein. Protein samples prepared from *E. coli* cultures carrying a plasmid with a c-erbB2 insert were analysed by SDS-PAGE and western blotting to ensure that the correct protein was being expressed.

Example 5

Detection of the Immune Response of Patients with Primary Breast Cancer Using a Panel Assay Methods:

(A) Preparation of Biotinylated Antigen

*E. coli* transformed with the appropriate PinPoint™ plasmid expressing biotinylated antigen were grown in a 5 ml overnight culture (LB+amp+biotin) and the overnight culture used to inoculate a 150 ml culture. The 150 ml culture was grown to OD 0.4-0.6 then expression of the fusion protein was induced by the addition of IPTG to a final concentration of 1 mM and the induced culture incubated at 25° C. The bacterial cells were harvested by centrifugation and then lysed by gentle sonication in a Tris/EDTA buffer containing the protease inhibitor PMSF. Cellular debris was removed by centrifugation at ~50,000 g and the resultant particle-free supernatant assayed by avidin ELISA to confirm the presence of biotinylated protein.

(B) c-erbB2/p53 Autoantibody Assay Method
1. Standard 96 well microtiter assay plates were coated with avidin, using 50 µl of a 1 µg/ml solution per well, and allowed to air dry overnight. The plates were then washed once with PBS/Tween to remove residual salt crystals, blocked for 60 minutes with a solution of 2% (w/v) PVP (polyvinylpyrolidone 360) in PBS and washed three times using PBS/Tween.

2. Particle free supernatant containing the appropriate biotinylated antigen (prepared as described in section (1) above) was plated out at 50 µl per avidin-coated well and then incubated for 60 minutes at room temperature with shaking to allow the biotin/avidin binding reaction to take place. The plates were then washed four times with PBS/Tween.

3. Serum samples to be tested for the presence of autoantibodies (diluted 1/50 and 1/100 in PBS) were plated out in triplicate (50 µl per well) and then incubated for 60 minutes with shaking to allow formation of any autoantibody/antigen complexes. Plates were then washed four times with PBS/Tween to remove unbound serum components.

4. 50 µl of ARP conjugated anti-human IgG/IgM antibody (obtained from Dako and used at a dilution recommended by the manufacturer) was added to each well and incubated for 60 minutes at room temperature with shaking. The plates were then washed again four times with PBS/Tween.

5. 50 µl of TMB was added to each well and measurements of OD at 650 nm for each well of the assay plate were taken kinetically over a period of 10 minutes.

For each antigen, control assays were performed following the procedure described above but using a sample of protein induced from *E. coli* transformed with a control PinPoint™ vector containing an out-offrame cDNA instead of the particle free supernatant containing biotinylated antigen. As it will be apparent to persons skilled in the art, the above methodology can be adapted for use in the detection of autoantibodies of any specificity with use of an appropriate biotinylated antigen.

(C) MUC1 Autoantibody Assay

1. ABC MUC1 isolated from the serum of patients with advanced breast cancer according to the method of Example 1 (all three fractions pooled) was diluted appropriately in PBS, plated out on a 96 well microtiter assay plate at 50 µl per well and left to dry overnight. The plate was then washed once with PBS/Tween to remove residual salt crystals, blocked for 60 minutes using a solution of 2% (w/v) PVP in PBS and washed three times with PBS/Tween.

2. Serum samples to be tested for the presence of autoantibodies (diluted 1/50 and 1/100 in PBS) were plated out in triplicate, adding 50 µl per well, and incubated for 60 minutes at room temperature with shaking. The plate was then washed four times with PBS/Tween.

3. 50 µl of HRP conjugated anti-human IgG/IgM antibody (obtained from Dako and used at a dilution recommended by the manufacturer) was added to each well and incubated for 60 minutes at room temperature with shaking. The plates were then washed again four times with PBS/Tween.

4. 50 µl of TMB was added to each well and measurements of OD at 650 nm for each well of the assay plate were taken kinetically over a period of 10 minutes.

Results

Pre-operative blood samples taken from 21 patients diagnosed with primary breast cancer were assayed for the presence of autoantibodies against MUC1, p53 and c-erbB2. The results of these assays are shown in FIG. 1 and summarised in Table 2.

TABLE 2

| Sample | anti-p53 | Prediction | anti-c-erbB2 | Prediction | anti-MUC I | Prediction | Combined |
|---|---|---|---|---|---|---|---|
| 1 | + | cancer | − | normal | + | cancer | CANCER |
| 2 | +/− | ? | +/−. | ? | +/− | ? | cancer |
| 3 | + | cancer | +/− | ? | + | cancer | CANCER |
| 4 | + | cancer | + | cancer | + | cancer | CANCER |
| 5 | + | cancer | + | cancer | +/− | ? | CANCER |
| 6 | − | normal | + | cancer | +/− | ? | cancer |
| 7 | + | cancer | + | cancer | + | cancer | CANCER |
| 8 | +/− | ? | + | cancer | +/− | ? | CANCER |
| 9 | + | cancer | + | cancer | + | cancer | CANCER |
| 10 | + | cancer | + | cancer | − | normal | CANCER |
| 11 | +/− | ? | + | cancer | + | cancer | CANCER |
| 12 | − | normal | + | cancer | − | normal | cancer |
| 13 | + | cancer | − | normal | + | cancer | CANCER |
| 14 | +/− | ? | + | cancer | + | cancer | CANCER |
| 15 | + | cancer | − | normal | + | cancer | CANCER |
| 16 | − | normal | − | normal | +/− | ? | ? |
| 17 | +/− | ? | − | normal | + | cancer | cancer |
| 18 | + | cancer | + | cancer | + | cancer | CANCER |
| 19 | + | cancer | + | cancer | + | cancer | CANCER |
| 20 | + | cancer | − | normal | + | cancer | CANCER |
| 21 | + | cancer | +/− | ? | − | normal | cancer |

FIG. 1 shows the results of the assays for autoantibodies specific to MUC1, c-erbB2 and p53. For each set of data the dotted line represents the cut-off value for normality. For the purposes of this study the normal control patients were women who clinically and/or mammographically had no evidence of breast cancer at the time of taking the serum sample. In order to establish the cut-off value for normality, control assays were performed on a total of 30 normal patients. Values below the dotted line fall within the normal control range and were scored as negative (−) in Table 2 whereas values above the dotted line were scored as positive (+). Values which were difficult to score as negative or positive with a reasonable degree of certainty were scored +/−. Patients scoring positive in at least two of the assays were identified as strongly positive for breast cancer (indicated "CANCER" in Table 2); patients scoring positive in at least one of the assays were identified as probable for breast cancer (indicated "cancer" in Table 2).

The results presented illustrate the predictive value of the three autoantibody assays both when used individually and when used as a panel. The use of a single assay to predict breast cancer gave approximately 40% of the results as a false negatives. However, by combining the results from all three assays only one patient appeared as a false negative (<5%), 71% of patients were scored as strongly positive for breast cancer (i.e. positive in at least two assays) and 23% of patients were scored as probable for breast cancer (i.e. positive in at least one assay). The results also show that a group of patients which have all been diagnosed with primary breast cancer have different serological profiles in terms of the immune response to their cancer. Thus, no single one of the three autoantibody assays would be useful in all primary breast cancer patients.

Example 6

Cloning of a ras Antigen

Method cDNA encoding a mutant oncogenic form of ras (designated K-ras) was cloned from the cell line KNRK (Rat kidney, Kirsten MSV transformed, see Aaronson, S. A. and Weaver, C. A. (1971) J. Gen. Virol. 13: 245-252; ATCC accession number CRL 1569). mRNA was extracted from the cell pellet using a Dynabead mRNA purification kit according to the manufacturer's recommended protocol cDNA synthesis, cloning into the EcoRV site of the PinPoint™ vector and transformation of E. coli was carried out as described in Example 4. Clones expressing ras were then identified by expression screening using the anti-ras antibody F234-4.2 from Calbiochem.

Example 7

Cloning of c-myc

Method cDNA encoding human c-myc was cloned from the breast cancer cell line T47-D (European Collection of Animal Cell Cultures accession number 85102201). mRNA was extracted from the cell pellet using a Dynabead mRNA purification kit according to the manufacturer's recommended protocol. cDNA synthesis, cloning into the EcoRV site of the PinPoint™ vector and transformation of E. coli was carried out as described in Example 4. Clones expressing c-myc were then identified by expression screening using the anti-cmyc antibody 4111.1 from Unilever.

Example 8

Assay for ras and c-myc Autoantibodies

Biotinylated c-myc and ras antigens were prepared from E. coli transformed with the appropriate PinPoint™ plasmid vector expressing biotinylated c-myc or biotinylated ras, as described in Example (5), part (A). The assays for c-myc and ras autoantibodies were then performed according to the protocol described in Example (5), part (B).

Example 9

Method of Detecting Recurrent Disease in a Patient Previously Diagnosed as Carrying Tumour Cells A group of nine patients previously diagnosed with primary breast cancer were selected. Pre-operative serum samples were taken from each of these patients prior to surgery for the removal of the primary breast cancer. Follow-up serum samples were then taken postoperatively at 2 or 3 monthly intervals and during the same period of time the patients were assessed clinically for signs of recurrent disease. None of the patients received any post-operative therapy until recurrence was diagnosed clinically. The pre-operative and post-operative serum samples from each of the patients were assayed for the presence of autoantibodies to MUC1, c-erbB2 and p53, using the assay methods described above under Example 5, and also for the presence of the commonly used serum tumour marker protein CA15-3. The results of these assays are summarised in Table 3 and results for three of the nine patients are presented graphically in FIG. 3. Clinical signs of recurrent disease were scored as follows:

| | |
|---|---|
| LN | recurrent disease in the lymph nodes |
| LR | local recurrence |
| METS | distant metastases present |

Results

In each of the patients at least one class of autoantibody was observed to remain above normal level. This suggests continued presence of the tumour marker (immunogen) and hence continued presence of tumour. Serum levels of the tumour marker protein CA15-3 were not found to be predictive of recurrent disease.

TABLE 3

| Patient | Sample date | CA 15-3 | Anti-p53 | Prediction | Anti c-erbB2 | Prediction | Anti MUCI | Prediction | Predicted | Recurrence | Date of first recurrence | DFI (months) |
|---|---|---|---|---|---|---|---|---|---|---|---|---|
| 0001 | December 1988 | 11 | − | | + | Cancer | + | Cancer | CANCER | — | | |
| | March 1987 | 12 | − | | + | Cancer | + | Cancer | CANCER | — | | |
| | May 1987 | 13 | − | | + | Cancer | + | Cancer | CANCER | — | | |
| | August 1987 | 22 | +/− | ? | + | Cancer | + | Cancer | CANCER | — | | |
| | November 1987 | 56 | +/− | ? | + | Cancer | + | Cancer | CANCER | METS | | |
| | December 1987 | 79 | +/− | ? | + | Cancer | + | Cancer | CANCER | METS | | 11 |
| 0002 | January 1987 | 16 | − | | + | Cancer | +/− | ? | Cancer | — | | |
| | May 1987 | 8 | − | | + | Cancer | +/− | ? | Cancer | — | | |
| | August 1987 | 10 | − | | + | Cancer | + | Cancer | CANCER | — | | |
| | November 1987 | 12 | +/− | ? | + | Cancer | + | Cancer | CANCER | — | | |
| | February 1988 | 16 | − | | + | Cancer | + | Cancer | CANCER | — | February 1989 | 23 |
| 0003 | February 1987 | 10 | − | | + | Cancer | − | | Cancer | — | | |
| | May 1987 | 7 | + | Cancer | + | Cancer | − | | CANCER | — | | |
| | August 1987 | 8 | + | Cancer | + | Cancer | − | | CANCER | — | | |
| | November 1987 | 12 | + | Cancer | + | Cancer | − | | CANCER | — | | |
| | February 1988 | 12 | + | Cancer | + | Cancer | − | | CANCER | — | | |
| | May 1988 | 11 | − | | + | Cancer | − | | Cancer | — | December 1989 | 34 |
| 0004 | February 1987 | 8 | + | Cancer | ++ | Cancer | − | | CANCER | — | | |
| | April 1987 | | + | Cancer | + | Cancer | − | | CANCER | — | | |
| | June 1987 | 4 | + | Cancer | + | Cancer | − | | CANCER | — | | |
| | December 1987 | 0.4 | + | Cancer | ++ | Cancer | − | | CANCER | — | | |
| | March 1988 | 7 | ++ | Cancer | ++ | Cancer | − | | CANCER | — | February 1993 | 71 |
| 0005 | March 1987 | 16 | +/− | ? | + | Cancer | − | | Cancer | — | | |
| | June 1987 | 13 | +/− | ? | + | Cancer | − | | Cancer | — | | |
| | September 1987 | 14 | + | Cancer | + | Cancer | +/− | ? | CANCER | — | | |
| | December 1987 | 17 | +/− | ? | + | Cancer | +/− | ? | CANCER | — | | |
| | March 1988 | 16 | | | | | | | | — | | |
| | May 1988 | | | | | | | | | LN | | 15 |

TABLE 3-continued

| Patient | Sample date | CA 15-3 | Anti-p53 | Prediction | Anti c-erbB2 | Prediction | Anti MUC1 | Prediction | Predicted | Recurrence | Date of first recurrence | DFI (months) |
|---|---|---|---|---|---|---|---|---|---|---|---|---|
| 0006 | May 1987 | 12 | − | | + | Cancer | + | Cancer | CANCER | — | | |
| | July 1987 | 15 | − | | + | Cancer | + | Cancer | CANCER | — | | |
| | September 1987 | 9 | +/− | ? | + | Cancer | +/− | ? | Cancer | LR | | 4 |
| | November 1987 | 12 | − | | + | Cancer | +/− | ? | Cancer | — | | |
| | March 1988 | 15 | − | | +/− | ? | − | | | — | | |
| | May 1988 | 13 | − | | +/− | ? | − | | | — | November | |
| 000& | June 1987 | 26 | + | Cancer | ++ | Cancer | − | | CANCER | — | | |
| | August 1987 | 28 | + | Cancer | + | Cancer | | | CANCER | — | | |
| | October 1987 | 42 | + | Cancer | + | Cancer | − | | CANCER | — | | |
| | December 1987 | 105 | + | Cancer | ++ | Cancer | + | Cancer | CANCER | METS | December | 6 |
| 0008 | June 1987 | 48 | + | Cancer | + | Cancer | + | Cancer | CANCER | — | | |
| | August 1987 | 30 | + | Cancer | + | Cancer | + | Cancer | CANCER | — | | |
| | October 1987 | 17 | + | Cancer | + | Cancer | + | Cancer | CANCER | — | | |
| | January 1988 | 14 | + | Cancer | + | Cancer | + | Cancer | CANCER | — | | |
| | May 1988 | 22 | + | Cancer | + | Cancer | +/− | ? | CANCER | LR | May 1988 | 11 |
| 0009 | May 1987 | 17 | − | | +/− | ? | − | | | — | | |
| | August 1987 | 17 | − | | + | Cancer | − | | Cancer | — | | |
| | November 1987 | 18 | − | | + | Cancer | − | | Cancer | LR | | 6 |
| | January 1988 | 31 | − | | + | Cancer | +/− | ? | Cancer | METS | | 8 |

Example 10

Retrospective Analysis of a Well Characterised Series of Healthy Controls and Patients with Early Breast Cancer The above-described methods for detecting autoantibodies to MUC1, p53, c-erbB2 and c-myc were used to carry out a retrospective study on a large number of early (stage 1 and 2) breast cancer sera as well as a large number of control serum samples from individuals with no evidence of malignancy (control group). The serum samples from patients were all taken within a 4 week pre-operative period. At the same time, the serum samples were assayed for the presence of circulating antigen (MUC1 and c-erbB2) using conventional tumour marker kits (used normally in advanced disease only). This would allow an assessment of whether the autoantibody assays are more sensitive than the conventional antigen assays. As used herein, the terms early or primary breast cancer means that the primary tumour has a diameter of less than 5 cm. Stage 1 early breast cancer is defined as lymph node negative; Stage 2 early breast cancer is defined as lymph node positive.

In total, pre-operative serum samples from 200 patients diagnosed with primary breast cancer and 100 normal control samples were assayed for autoantibodies against MUC1, p53, c-erbB2 and c-myc. The results are summarised in Tables 4-7 and FIGS. 4-7.

FIG. 4 depicts the range of autoantibody levels found for each assay in normal individuals and patients with early breast cancer. It is apparent that cancer patients have a considerably higher level of circulating autoantibodies to these markers than do normal individuals. Using the range for the normal individuals it is possible to set a 'cut-off' above which no normal values should lie. Therefore, samples with autoantibody levels above this cut-off can be deemed to be positive for cancer. Cut-off points determined in this manner were used to score the results of the retrospective study in early breast cancer patients.

The results presented in Tables 4-7 and FIGS. 5-7 demonstrate the predictive value of the four autoantibody assays both individually and when used in combination as a panel of assays. Table 4 indicates the increased sensitivity of combining the results of a number of assays. By using one assay on its own, less than 50% of cancers are detected, however the power of detection increases as more assays are added to the panel until the combination of all four assays allows 82% of primary cancers to be detected. FIG. 7 shows the percentage of samples which are positive in 0 out of 4 assays up to 4 out of 4 assays. This provides good evidence that the panel assay is more powerful in the detection of cancer than any one single marker assay since not all patients with cancer have raised autoantibodies to all markers.

Tables 5-7 summarise the detection rates in stage 1, stage 2 and in early breast cancer (i.e. stage 1 and 2) for various combinations of autoantibody assays. The use of a single autoantibody assay to predict breast cancer gives approximately 60-70% of the results as false negatives in the stage 1 group; and 50-60% in stage 2. However, by combining the results from all four assays, 76% of stage 1 and 89% of stage 2 cancers were positive in one or more assay. The overall detection rate for early breast cancer (i.e. both stage 1 and stage 2 cancers) using this system was 82%. In both stage 1 and stage 2 cancer, assaying for autoantibodies to MUC1 appeared to add predictive power to any combination of assays.

The results for this study were obtained using a 100% confidence limit, in other words for a result to be deemed positive it had to fall above the cut-off for readings in the normal range. This normal range was previously evaluated from a large number of normal individuals and then confirmed using the control group of 100 normal individuals mentioned above. Therefore, within the normal control group, none of the samples were found to be positive, meaning that the sensitivity of the panel of autoantibody assays was 100% for the detection of early breast cancer (FIG. 5).

FIGS. 6 and 7 demonstrate the detection rates which are achievable if specificity is reduced from a 100% confidence level (no false positives) to a 95% confidence level, where some degree of false positive detection is expected. In this case, the cut-off point is defined as the mean value plus twice the standard deviation of the normal sample range. Using this cut-off point, approximately 5% of the normal samples were determined to be positive for cancer (i.e. false positives); whilst detection of primary cancer increased to approximately 94% (i.e. 6% false negatives). Again, the greatest percentage of the sample group were positive in only 1 out of the 4 assays, however, the percentage of samples that were positive in all 4 assays increased considerably.

Since the above study was carried out retrospectively, clinical data was available regarding the initial diagnosis as well as clinical data regarding the post-operative outcome (i.e. follow-up data). This allowed analysis of the prognostic value of the data obtained from the autoantibody assays. Table B shows the correlations between serum levels of autoantibodies to MUC1, p53, c-erbB2 and c-myc and a number of clinical factors. For instance, the presence of autoantibodies to any of the 4 tumour associated proteins (MUC1, p53, c-erbB2 or c-myc) appears to correlate with the development of a recurrence. In other words, those patients who had autoantibodies were more likely to go on to develop a recurrence of their disease. In the case of autoantibodies to MUC1, c-myc and c-erbB2, this was most likely to be distant metastases, only autoantibodies to p53 were not associated with the later development of distant metastases with any statistical significance. In fact, the presence of autoantibodies to p53 was the weakest indicator of a later recurrence of disease; furthermore, p53 autoantibodies correlated with disease free interval.

Table 9 presents an analysis of whether the degree of autoantibody positivity may be of value in the prediction of which stage 1 tumour will go on to develop a recurrence. At the present time, there is little to indicate at the time of diagnosis whether a patient with a stage 1 tumour (i.e. no evidence of spread of tumour to the lymphatic system) will go on to develop recurrent disease. As can be seen in Table 9, of those patients with stage 1 tumours from the sample group that went on to develop recurrent disease, 71% were positive in two or more autoantibody assays. Of the patients with stage 1 tumours that have not yet recurred, only 30% were positive in two or more autoantibody assays.

TABLE 4

Sensitivity of autoantibody assays in the detection of early breast cancer.

|  | % PBC positive |
|---|---|
| Single marker assay | 35-47 |
| Two marker assay | 51-60 |
| Three marker assay | 63-76 |
| Four marker assay | 82 |

TABLE 5

Sensitivity of autoantibody panel assays in the detection of stage 1 breast cancer.

|  | p53 | c-erbB2 | c-myc | MUC1 |
|---|---|---|---|---|
| p53 | 38 | 48 | 58 | 59 |
| c-erbB2 |  | 31 | 50 | 51 |
| c-myc |  |  | 41 | 55 |
| MUC1 |  |  |  | 38 |
| p53/c-erbB2 |  |  | 61 | 66 |
| p53/c-myc |  |  |  | 73 |
| c-erbB2/c-myc |  |  |  | 65 |
| p53/c-erbB2/c-myc |  |  |  | 76 |

TABLE 6

Sensitivity of autoantibody panel assays in the detection of stage 2 breast cancer.

|  | p53 | c-erbB2 | c-myc | MUC1 |
|---|---|---|---|---|
| p53 | 40 | 56 | 55 | 73 |
| c-erbB2 |  | 42 | 56 | 73 |
| c-myc |  |  | 33 | 69 |
| MUC1 |  |  |  | 56 |
| p53/c-erbB2 |  |  | 65 | 84 |
| p53/c-myc |  |  |  | 80 |
| c-erbB2/c-myc |  |  |  | 84 |
| p53/c-erbB2/c-myc |  |  |  | 89 |

TABLE 7

Sensitivity of autoantibody panel assays in the detection of primary breast cancer.

|  | p53 | c-erbB2 | c-myc | MUC1 |
|---|---|---|---|---|
| p53 | 38 | 51 | 57 | 64 |
| c-erbB2 |  | 35 | 53 | 59 |
| c-myc |  |  | 37 | 60 |
| MUC1 |  |  |  | 47 |
| p53/c-erbB2 |  |  | 63 | 73 |
| p53/c-myc |  |  |  | 76 |
| c-erbB2/c-myc |  |  |  | 72 |
| p53/c-erbB2/c-myc |  |  |  | 82 |

TABLE 8

Correlations between serum autoantibody level and various clinical factors.

| FACTOR | MUC1 | p53 | c-erbB2 | c-myc |
|---|---|---|---|---|
| recurrence | ✓ | 1/4 | ✓ | ✓ |
| local recurrence | 1/2 | 1/2 | 1/2 | 1/4 |
| distant metastases | ✓ | X | ✓ | ✓ |
| stage | X | X | X | X |
| grade | X | X | X | X |
| family history | X | X | X | X |
| disease free interval | X | ✓ | X | X |
| age | X | X | X | X |
| menopausal status | X | X | X | X |

Key:
✓ Good correlation
1/2 Moderate correlation
1/4 Weak correlation
X No correlation

TABLE 9

Analysis of the degree of positivity in autoantibody assays for recurrent and non-recurrent stage 1 breast cancer tumours.

|  | Negative-no autoantibodies detected | +ve auto-antibodies to one marker | +ve auto-antibodies to 2-4 markers |
|---|---|---|---|
| Recurrent | 12% | 17% | 71% |
| Non-recurrent | 22% | 48% | 30% |

Example 11

Detection of Autoantibodies in Sequential Serum Samples—Application to the Monitoring of Disease Progression This study was carried out in order to assess whether autoantibody assays could be useful in the earlier detection of recurrent disease.

Levels of autoantibodies to MUC1, p53 and c-erbB2 in the serum of patients previously diagnosed with breast cancer were measured sequentially during follow-up until the patient manifested recurrent disease. The results are summarised in FIGS. 8-10. All three patients went on to develop recurrent disease. In all three patients, autoantibody levels were indicative of the presence of cancer. However, there is no evidence from this group that autoantibody levels decrease after removal of the primary tumour. FIG. 10 shows the levels of autoantibodies post-operatively of a patient with non-recurrent disease and a patient with recurrent disease. Autoantibody levels in the patient with non-recurrent disease remained below the cut-off point during the period of sample collection (48 months). In the second patient, whose disease recurred at 36 months, autoantibody levels are seen to be steadily rising towards the cut-off point, with c-erbB2 autoantibodies rising above cut-off. Furthermore, as can be seen in FIG. 9, when further sequential samples are added to the analysis, 3 out of the 4 assays become positive for cancer and these levels then decrease again once treatment of the recurrence is underway. This data supports the utility of autoantibody assays in the earlier detection of recurrent disease.

Example 12

Analysis of a Series of Patients with Bladder Cancer and Benign Urological Disorders Serum samples were collected from a group of 80 patients with bladder cancer/benign urological disorders and analysed for the presence of autoantibodies to MUC1, p53, c-erbB2 and c-myc using the assay methods described above.

The data summarised in Table 10 shows that single assay sensitivities for bladder cancer detection range from 15-50% (as opposed to 35-47% for breast cancer). The detection sensitivity using all 4 assays was 80%, similar to that found for early breast cancer.

FIG. 11 shows the break down of detection rates between urologically benign disorders ('benign') and the three stages of bladder cancer. Upon further investigation of the relevant clinical data it became apparent that 6 of the patients in the 'benign' group had evidence of other malignancies. These other malignancies were lung cancer, skin cancer and adenocarcinoma. Evidence of other malignancies were: pleural effusion, ovarian cysts and colon polyps. Serum samples from all 6 of these patients had been scored as positive for cancer using the panel of autoantibody assays, illustrating the general application of the panel assay to the detection of cancers. Furthermore, it is known that some patients with stage PT1/2 and PT3/4 disease had previously received systemic therapy.

TABLE 10

Sensitivity of autoantibody assays in the detection of bladder cancer.

|  | % positive |
|---|---|
| Single marker assay | 15-50 |
| Two marker assay | 28-73 |
| Three marker assay | 46-76 |
| Four marker assay | 80 |

TABLE 11

Sensitivity of autoantibody panel assays in the detection of bladder cancer.

|  | p53 | c-erbB2 | c-myc | MUC1 |
|---|---|---|---|---|
| p53 | 50 | 73 | 73 | 73 |
| c-erbB2 |  | 17 | 28 | 36 |
| c-myc |  |  | 15 | 35 |
| MUC1 |  |  |  | 24 |
| p53/c-erbB2 |  |  | 76 | 76 |
| p53/c-myc |  |  |  | 75 |
| c-erbB2/c-myc |  |  |  | 46 |
| p53/c-erbB2/c-myc |  |  |  | 80 |

Example 13

Sensitivity of Autoantibody Assay in Diagnosis of Colorectal Cancer

An autoantibody assay as previously described was carried out on serum samples from patients with colorectal cancer using the tumour antigens c-myc, p53, c-erbB2 and K-ras individually and as a panel. The results are shown in FIGS. 12 and 13. As has been demonstrated previously increased sensitivity is shown when a panel of antigens is used.

Example 14

Use of BRCA1 in Panel Assay for Detection of Breast Cancer

A BRCA1 antigen suitable for use in the detection of anti-BRCA1 autoantibodies was cloned from the breast cancer cell line MCF7 using an RT-PCR strategy. Briefly, mRNA isolated from MCF7 cells was reverse transcribed to give first-strand cDNA. These cDNA was used as a template for PCR using a primer pair designed to amplify a product covering the first 1500 base pairs of the BRCA1 cDNA but including a known mis-match mutation that leads to an early stop codon and therefore the production of truncated protein. Different sites for restriction enzyme digestion were also incorporated into the forward and reverse PCR primers to facilitate the cloning of the PCR product. The PCR primers were as follows:

```
                                         (SEQ. ID. NO. 1)
5'-GAC AGG ATC CGG ATG GAT TTA TCT GCT CTT

CGC GTT G
                                         (SEQ. ID. NO. 2)
5'-GCG GCC GCC CTC ATG TAG GTC TCC TTT TAC

GC
```

The PCR product obtained using these primers was then cloned into the PinPoint™ vector and used to transform *E. coli* Top 10 F cells, as described hereinbefore. Clones expressing the fusion protein of truncated BRCA1 antigen fused in-frame to the N-terminal biotinylation domain were then identified by expression screening, according to the procedure described in Example 4, using the antibody MAB4132 from Chemicon.

Biotinylated truncated BRCA1 antigen is then prepared from *E. coli* transformed with the appropriate PinPoint™ plasmid vector expressing the fusion protein, as described in Example (5), part (A). The assay for BRCA1 autoantibodies is then performed according to the protocol described in Example (5), part (B).

FIG. 14 shows the results of a study in which the above-described assays for autoantibodies to cmyc, p53, c-erbB2, MUC1 and BRCA1 were performed individually, as a panel and as a panel without BRCA1 to detect autoantibodies in samples of serum taken from normal individuals, patients diagnosed with primary breast cancer and BRCA1 mutation carriers. As demonstrated previously, increased sensitivity is shown when a panel of markers is used.

Example 15

Use of Autoantibody Panel Assay for Detecting Prostate Cancer, Incorporating PSA cDNA encoding human PSA was cloned from the cell line T47-D using a protocol similar to that described above for the cloning of c-erbB2. Briefly, the T47-D cells were first stimulated with Apigenin at 10-5M as described by Rosenberg et al. (1998) *Biochem Biophys Res Commun.* 248: 935-939. mRNA was then extracted and cDNA synthesis, ligation into PinPoint™ and transformation of *E. coli.* performed as described in Example 4. Clones expressing PSA were identified using an anti-PSA antibody. Biotinylated PSA antigen was prepared from *E. coli* transformed with the PinPoint™ vector expressing biotinylated PSA according to the protocol described in Example (5), part (A). The assay for PSA autoantibodies was then performed according to the protocol described in Example (5), part (B).

An autoantibody assay using the methods described above was carried out on patients with prostate cancer using c-myc, p53, c-erbB2, PSA and MUC 1 individually and as a panel. The results are shown in FIG. 15 and confirm the increased sensitivity of such a panel for detection of prostate cancer.

Example 16

Other Tumour Marker Antigens

CA125 can be affinity purified from the ovarian cancer cell line OVRCAR-3 (available from the ATCC) using Mab VK-8, as described by Lloyd, K. O. et al. (1997) *Int. J. Cancer.* 71: 842-850.

APC protein is expressed by the colorectal cancer cell line SW480 (available from the ATCC) as described by Munemitsu, S. et al. (1995) *PNAS* 92: 3046-3050.

The invention claimed is:

1. A method of detecting the immune response of a mammal to circulating tumour marker proteins or tumour cells expressing the tumour marker proteins comprising:
   (a) diluting a sample of bodily fluids from the mammal;
   (b) contacting the diluted sample of bodily fluids from step (a) with a panel of two or more tumour marker antigens immobilized on a solid support, wherein at least one of the two or more tumour antigens is selected from the group consisting of MUC1, p53, c-erbB2, Ras, c-myc, BRCA1, BRCA2, PSA, APC and CA125, wherein the two or more tumor marker antigens are recombinantly produced; and
   (c) detecting autoantibody-antigen complexes by contacting said complexes with labeled anti-IgG and/or labeled anti-IgM to determine the presence or absence of complexes of the tumour marker antigens bound to autoantibodies present in the sample of bodily fluids, the autoantibodies being immunologically specific to the tumour marker proteins;

whereby the presence of the complexes is indicative of the immune response to circulating tumor marker proteins or tumour cells expressing the tumour marker proteins.

2. The method of claim 1 wherein the panel comprises p53 and c-erbB2.

3. The method of claim 2 wherein the complexes detected are indicative of cancer, the cancer is breast cancer, and the panel also includes at least one tumour marker antigen selected from the group consisting of MUC1, c-myc, BRCA1, BRCA2, and PSA.

4. The method of claim 1 wherein the cancer is bladder cancer and the panel is selected from at least two tumour marker antigens selected from the group consisting of p53, c-erbB2, MUC1 and c-myc.

5. The method of claim 1 wherein the cancer is colorectal cancer and the panel is selected from at least two tumour marker antigens selected from the group consisting of p53, Ras, c-erbB2 and APC.

6. The method of claim 1 wherein the cancer is prostate cancer and the panel is selected from at least two tumour marker antigens selected from the group consisting of p53, PSA, BRCA1 and c-erbB2.

7. The method of claim 1 wherein the cancer is ovarian cancer and the panel is selected from at least two tumour marker antigens selected from the group consisting of p53, CA125, c-erbB2 and BRCA1.

8. The method of claim 1 wherein the cancer is breast cancer and the panel is selected from at least two tumour marker antigens selected from the group consisting of p53, MUC1, c-erbB2, c-myc, BRCA1, BRCA2 and PSA.

9. A method of determining the immune response of a patient to two or more circulating tumour marker proteins or to tumour cells expressing the tumour marker proteins and identifying which one of the two or more tumour marker proteins elicits the strongest immune response in the patient, comprising:
  (a) diluting a sample of bodily fluids from the patient;
  (b) contacting the diluted sample of bodily fluids from step (a) with a panel of two or more distinct tumour marker antigens immobilized on a solid support, wherein the two or more tumour marker antigens are recombinantly produced;
  (c) measuring the amount of complexes formed by binding of each of the tumour marker antigens to autoantibodies present in the sample of bodily fluids, the autoantibodies being immunologically specific to the tumour marker proteins; whereby the presence of the complexes is indicative of the immune response to circulating tumour marker proteins or tumour cells expressing the tumour marker proteins,
  wherein the measurement obtained acts as an indicator of the relative strength of the immune response to each tumour marker protein and thereby identifies which one of the tumour marker proteins elicits the strongest immune response in the patient wherein at least one of the tumour marker antigens is selected from the group consisting of MUC1, c-erbB2, c-myc, Ras, p53, BRCA1, BRCA2, PSA, APC or CA125.

10. The method of claim 9 wherein the relative strength of the immune response to each of the tumour marker proteins or tumor cells indicates selection of a course of anti-cancer treatment.

11. The method of claim 10 wherein one or more tumour marker proteins identified as eliciting a strong immune response in the patient indicate selection of the course of the anti-cancer treatment.

12. A method of detecting the immune response of a mammal to circulating tumour marker proteins or tumour cells expressing the tumour marker proteins comprising:
  (a) diluting a sample of bodily fluids from the mammal;
  (b) contacting the diluted sample of bodily fluids from step (a) with a panel of two or more distinct tumour marker antigens immobilized on a solid support, wherein the two or more tumour marker antigens are recombinantly produced;
  (c) determining the presence or absence of complexes of the tumour marker antigens bound to autoantibodies present in the sample of bodily fluids, the autoantibodies being immunologically specific to the tumour marker proteins;
  whereby the presence of the complexes is indicative of the immune response to circulating tumour marker proteins or tumour cells expressing the tumour marker proteins
  further comprising quantifying the immune response of a mammal to circulating tumour marker proteins or tumour cells expressing the tumour marker proteins wherein at least one of the tumour marker proteins is selected from the group consisting of c-erbB2, Ras, c-myc, p53, BRCA1, BRCA2, APC, PSA and CA125, and wherein the method further comprises
  measuring the quantity of complexes formed by binding of at least one tumour marker antigen to autoantibodies present in the sample of bodily fluids, the autoantibodies being immunologically specific to the tumour marker protein;
  wherein the measurement of the quantity of complexes indicates the amount of the autoantibodies present in the sample.

13. The method of claim 12 wherein the amount of autoantibodies present identifies those individuals who are at increased risk of developing cancer in a population of asymptomatic individuals.

14. A method for the detection of cancer comprising:
  (a) diluting a sample of bodily fluids;
  (b) contacting the diluted sample of bodily fluids from step (a) with a panel of two or more tumor marker antigens immobilized on a solid support selected from the group consisting of c-erbB2, ras, biotinylated c-myc, BRCA1, BRCA2, APC, PSA, CA125 and biotinylated p53 or antigentic fragments thereof, wherein the two or more tumour marker antigens or antigentic fragments are recombinantly produced;
  (c) measuring the quantity of complexes formed by binding of at least one tumour marker antigen to autoantibodies present in the sample of bodily fluids, the autoantibodies being immunologically specific to the tumour marker protein; and
  (d) using the measurement obtained in (b) as an indicator of the amount of the autoantibodies present in the sample.

15. The method of claim 14 wherein the cancer is recurrent disease in a patient previously diagnosed as carrying tumour cells, wherein the patient has undergone treatment to reduce the number of the tumour cells.

16. The method of claim 15 wherein the amount of autoantibodies present monitors the progress of neoplastic disease.

17. The method of claim 15 wherein the amount of autoantibodies present predicts the response of the patient with cancer to anti-cancer treatment.

18. The method of claim 17 wherein the anti-cancer treatment is hormone therapy, chemotherapy, radiotherapy, anti-growth factor therapy, immune therapy or vaccination.

19. A method for the detection of the recurrence of cancer, wherein the cancer is early neoplastic or early carcinogenic change in an asymptomatic patient comprising:
(a) diluting a sample of bodily fluids;
(b) contacting the diluted sample of bodily fluids from step (a) with at least two tumour marker antigens immobilized on a solid support selected from the group consisting of c-erbB2, ras, biotinylated c-myc, BRCA1, BRCA2, APC, PSA, CA125 and biotinylated p53 or antigenic fragments thereof, wherein the two or more tumour marker antigens or antigentic fragments are recombinantly produced;
(c) measuring the quantity of complexes formed by binding of the tumour marker antigens to autoantibodies present in the sample of bodily fluids, the autoantibodies being immunologically specific to tumour marker proteins; and
(d) using the measurement obtained in (b) as an indicator of the amount of the autoantibodies present in the sample,
wherein the cancer is recurrent disease in a patient previously diagnosed as carrying tumour cells, and wherein the patient has undergone treatment to reduce the number of the tumour cells.

20. A method of detecting the immune response of a mammal to circulating tumour marker proteins or tumour cells expressing the tumour marker proteins wherein the tumour marker proteins are MUC1, p53, c-erbB2, Ras, c-myc, BRCA1, BRCA2, PSA, APC or CA125, the method comprising:
(a) diluting a sample of bodily fluids from the mammal;
(b) contacting the diluted sample of bodily fluids from step (a) with two or more of MUC1, p53, c-erbB2, Ras, c-myc, BRCA1, BRCA2, PSA, APC or CA125 or antigenic fragments thereof immobilized on a solid support, wherein the two or more tumour marker antigens or antigenic fragments are recombinantly produced; and,
(c) detecting autoantibody-antigen complexes by contacting said complexes with labeled anti-IgG and/or labeled anti-IgM to determine the presence or absence of complexes of the tumour marker proteins or antigenic fragments thereof bound to autoantibodies present in the sample of bodily fluids, the autoantibodies being immunologically specific to the tumour marker proteins or antigenic fragments thereof;
whereby the presence of the complexes is indicative of the immune response to circulating tumor marker proteins or tumour cells expressing the tumour marker proteins.

21. The method of claim 20 wherein the presence of complexes indicates the presence of cancer.

22. The method of claim 21 wherein the cancer is early neoplastic or early carcinogenic change in asymptomatic patients.

23. The method of claim 21 wherein the cancer is recurrent disease in a patient previously diagnosed as carrying tumour cells, wherein the patient has undergone treatment to reduce the number of the tumour cells.

24. The method of claim 21 wherein the presence of complexes indicates the progress of cancer or other neoplastic disease.

25. The method of claim 21 wherein the presence of complexes identifies those individuals who are at increased risk of developing cancer in a population of asymptomatic individuals.

26. A method for the determination of the tumour marker profile of an individual suffering from cancer, wherein the cancer is neoplastic or early carcinogenic change in an asymptomatic patient, comprising:
(a) diluting a sample of bodily fluids from the individual;
(b) contacting the diluted sample of bodily fluids from step (a) with a panel of two or more distinct tumour marker antigens immobilized on a solid support, wherein the two or more tumour marker antigens are recombinantly produced;
(c) determining the presence or absence of complexes of the tumour marker antigens bound to autoantibodies present in the sample of bodily fluids, the autoantibodies being immunologically specific to the tumour marker proteins;
wherein the presence of the complexes is indicative of the tumour marker profile of the individual.

27. A method for the determination of the tumour marker profile of a patient at increased risk of recurrent cancer in a population of asymptomatic individuals, wherein the patient was previously diagnosed as carrying cancer cells and wherein the patient has undergone treatment to reduce the number of the cancer cells, comprising:
(a) diluting a sample of bodily fluids from the patient;
(b) contacting the diluted sample of bodily fluids from step (a) with a panel of two or more distinct tumour marker antigens immobilized on a solid support, wherein the two or more tumour marker antigens are recombinantly produced;
(c) determining the presence or absence of complexes of the tumour marker antigens bound to autoantibodies present in the sample of bodily fluids, the autoantibodies being immunologically specific to the tumour marker proteins;
wherein the presence of the complexes is indicative of the tumour marker profile of the patient.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Synthetic

<400> SEQUENCE: 1
gacaggatcc ggatggattt atctgctctt cgcgttg                              37

<210> SEQ ID NO 2
<211> LENGTH: 32
<212> TYPE: DNA
<213> ORGANISM: Artificial Sequence
<220> FEATURE:
<223> OTHER INFORMATION: Synthetic

<400> SEQUENCE: 2
gcggccgccc tcatgtaggt ctccttttac gc                                   32
```